(12) United States Patent
Cockrem et al.

(10) Patent No.: US 6,982,026 B2
(45) Date of Patent: Jan. 3, 2006

(54) AZEOTROPIC DISTILLATION PROCESS FOR PRODUCING ORGANIC ACIDS OR ORGANIC ACID AMIDES

(75) Inventors: Michael Charles Milner Cockrem, Madison, WI (US); Istvan Kovacs, Madison, WI (US)

(73) Assignee: Tate & Lyle Ingredients Americas, Inc., Decatur, IL (US)

( * ) Notice: Subject to any disclaimer, the term of this patent is extended or adjusted under 35 U.S.C. 154(b) by 206 days.

(21) Appl. No.: 09/809,649

(22) Filed: Mar. 15, 2001

(65) Prior Publication Data

US 2003/0029712 A1 Feb. 13, 2003

(51) Int. Cl.
*B01D 3/36* (2006.01)
*B01D 3/38* (2006.01)
*C07C 59/08* (2006.01)
*C07C 249/14* (2006.01)
*C12P 7/56* (2006.01)

(52) U.S. Cl. ............... 203/2; 203/63; 203/68; 203/69; 203/70; 203/73; 203/78; 203/79; 203/92; 203/93; 203/94; 203/95; 203/97; 203/DIG. 11; 562/589; 435/139; 210/774; 528/500; 528/501; 560/352

(58) Field of Classification Search ............. 203/1, 203/2, 14, 15, 52, 57, 63, 68, 69, 70, 42, 203/43, 100, 91, DIG. 11, 92, 93, 94, 95, 203/97, 73, 78, 79; 562/580, 589; 435/139, 435/136; 528/501, 500, 354; 560/352; 210/774, 210/656

See application file for complete search history.

(56) References Cited

U.S. PATENT DOCUMENTS 321,925 A 7/1885 Waite .................. 203/95
3,419,478 A 12/1968 Izard .................... 203/70

(Continued)

FOREIGN PATENT DOCUMENTS

| WO | 97/29068 | * | 8/1997 |
| WO | WO98/24777 | | 6/1998 |
| WO | 98/45239 | * | 10/1998 |
| WO | WO98/55442 | | 10/1998 |
| WO | WO99/19290 | | 4/1999 |
| WO | WO00/64850 | | 11/2000 |

OTHER PUBLICATIONS

Perry et al "Distillation", Technique of Organic Chemistry, vol. Iv, 1965, p. 481.*

(Continued)

*Primary Examiner*—Virginia Manoharan
(74) *Attorney, Agent, or Firm*—Williams, Morgan & Amerson, P.C.

(57) ABSTRACT

Disclosed herein are methods for the recovery of at least one of an organic acid or an organic acid amide, such as a heat stable lactic acid or lactamide, from a feed stream which contains the organic acid and/or organic acid amide. The feed stream is mixed with at least one azeotroping agent. The azeotroping agent is a hydrocarbon capable of forming at least one heteroazeotrope with the organic acid or the organic acid amide in the feed stream. The mixture of the feed stream and the azeotroping agent is heated to produce a vapor stream. The heteroazeotrope is a component of that vapor stream. The vapor stream can be heated further to separate components or it can be condensed into a liquid stream. The liquid stream is capable of being separated into a first phase and a second phase. The first phase contains the highest concentration of the organic acid and/or the organic acid amide and the azeotroping agent is part of the second phase. The liquid stream can be further distilled or, alternatively, the two phases of the liquid stream can be separated. The first phase can be removed from the remainder of the liquid stream resulting in recovery of the organic acid and/or organic acid amide. The recovered organic acid and/or organic acid amide can be further purified and/or concentrated from the first phase.

58 Claims, 2 Drawing Sheets

U.S. PATENT DOCUMENTS

| | | | | |
|---|---|---|---|---|
| 3,432,401 A | * | 3/1969 | Tcherkawsky | 203/15 |
| 3,718,545 A | * | 2/1973 | Horlenko | 203/15 |
| 3,772,157 A | * | 11/1973 | Horsley | 203/52 |
| 4,100,189 A | | 7/1978 | Mercier | 260/541 |
| 4,275,234 A | | 6/1981 | Baniel et al. | 562/584 |
| 5,068,418 A | | 11/1991 | Kulprathipanja et al. | 562/580 |
| 5,068,419 A | | 11/1991 | Kulprathipanja et al. | 562/580 |
| 5,138,074 A | | 8/1992 | Bellis et al. | 549/274 |
| 5,142,023 A | | 8/1992 | Gruber et al. | 528/354 |
| 5,264,086 A | * | 11/1993 | Berg et al. | 203/68 |
| 5,319,107 A | | 6/1994 | Benecke et al. | 549/274 |
| 5,510,526 A | | 4/1996 | Baniel et al. | 562/580 |
| 5,574,180 A | | 11/1996 | McQuigg et al. | 558/147 |
| 5,641,406 A | | 6/1997 | Sarhaddar et al. | 210/656 |
| 5,780,678 A | | 7/1998 | Baniel et al. | 562/580 |
| 5,831,122 A | | 11/1998 | Eyal | 562/580 |
| 5,945,560 A | * | 8/1999 | Iffland et al. | 560/205 |
| 5,959,144 A | | 9/1999 | Baniel | 562/580 |
| 6,087,532 A | | 7/2000 | Baniel et al. | 562/580 |
| 6,160,173 A | | 12/2000 | Eyal et al. | 562/589 |
| 6,187,951 B1 | | 2/2001 | Baniel et al. | 562/580 |
| 6,280,985 B1 | | 8/2001 | Caboche et al. | 435/139 |
| 6,489,508 B1 | | 12/2002 | Van Gansbeghe et al. | 562/589 |

OTHER PUBLICATIONS

Perry, "Azeotropic Distillation"; *Chemical Engineers' Handbook, Fifth Edition*, 13:36–42, 1973.

Holten, "Lactic acid; properties and chemistry of lactic acid and derivatives", pp. 20–21, p. 36–37, and p. 425, 1971.

CRC Handbook of Chemistry and Physics, pps. D1–D33, 1981–1982.

Co–pending U.S. Appl. No. 09/809,534; Entitled: "Azeotropic Distillation of Cyclic Esters of Hydroxy Organic Acids"; filed Mar. 15, 2001.

Co–pending U.S. Appl. No. 09/809,243; Entitled: "Process for Obtaining an Organic Acid from an Organic Acid Ammonium Salt, an Organic Acid Amide, or an Alkylamine–Organic Acid Complex"; filed Mar. 15, 2001.

* cited by examiner

AZEOTROPIC DISTILLATION PROCESS FOR PRODUCING ORGANIC ACIDS OR ORGANIC ACID AMIDES

BACKGROUND OF THE INVENTION

1. Field of the Invention

The present invention relates generally to processes for producing and recovering organic acids, such as lactic acid, and/or organic acid amides, such as lactamide. More particularly, it concerns methods that rely on azeotropic distillation for production and recovery of organic acids and/or organic acid amides.

2. Description of Related Art

Organic acids such as lactic acid have a number of commercial uses, for example in food manufacturing, pharmaceuticals, plastics, textiles, and as a starting material in various chemical processes. The current market in the United States for one organic acid, namely lactic acid, is about 50,000 tons per year, more than half of which is imported. It is well known to produce organic acids by fermentation of sugars, starch, or cheese whey, using microorganisms such as *Lactobacillus delbrueckii* to convert monosaccharides such as glucose, fructose, or galactose, or disaccharides such as sucrose, maltose, or lactose, into organic acids such as lactic acid. The broth that results from fermentation contains unfermented sugars, carbohydrates, amino acids, proteins, and salts, as well as the acid. Some of these materials cause an undesirable color or can interfere with downstream processing of the organic acid. The acid usually therefore must be recovered from the fermentation broth and in some cases must undergo further purification before it can be used.

Commercial uses of organic acid amides such as acetamide, formamide, and lactamide are typically as starting materials for various chemical processes. For example, formamide is used commercially as a solvent for certain materials due to its strong hydrogen bonding capability. Organic acid amides can be formed by heating an ester of an organic acid in the presence of ammonia. Organic acid amides can also be formed by heating the ammonium salt of an organic acid. For example, acetamide can be produced in this way. Formamide can be produced in a variety of ways. One method that can be used to produce formamide involves heating lactamide in the presence of formic acid.

Lactic acid and other α-hydroxyacids exist in two different optical isomers. For the example of lactic acid, these isomers are L-(+)-lactic acid and D-(−)-lactic acid. An equal mixture of D and L lactic acids is called a racemic mixture. It is often desirable to produce lactic acid with a high proportion of only one of the optical isomers. Different microorganisms used in fermentations to produce organic acids can produce different proportions of optical isomers of a particular organic acid. Chemical synthesis to prepare a higher proportion of a particular optical isomer can be difficult. It is desirable to minimize reactions that lead to the conversion of L-(+)-lactic acid into D-(−)-lactic acid and vice versa, so called racemization reactions. (L-(+)-lactic acid is also designated as S-(+)-lactic acid. D-(−)-lactic acid is also designated as R-(−)-lactic acid.) Exposing lactic acid solutions to relatively high temperatures can increase certain racemization reactions.

Lactamide and certain other substituted amides can exist in two different optical isomeric forms. For the example of lactamide, which is the amide typically formed from ammonia and lactic acid, these isomers are S-(−)-lactamide and R-(+)-lactamide. An equal mixture of R and S lactamides is called a racemic mixture. Note that the (+) and (−) designation refer to the optical rotation of a beam of polarized light that is passed through a standardized solution of the chemical, while the R and S notation refer to the stereo-specific configuration of the molecule. Thus, when S-(+)-lactic acid is converted to lactamide, the resultant lactamide is S-(−)-lactamide.

During the production of an organic acid such as lactic acid by fermentation, the increasing concentration of the acid in the fermentation broth reduces the pH. As the pH decreases, the growth of the microorganism is inhibited and eventually stops, and therefore acid production stops. To prevent this, the pH of the fermentation broth typically is controlled by adding a base for neutralization, such as ammonia or a sodium or calcium base. However, one result of the addition of such a base is the formation of a salt of the acid (e.g., ammonium lactate). Therefore, it is often necessary to convert the salt to free acid or another form such as an ester, which subsequently can be converted to the free acid.

Lactic acid is one organic acid of particular interest today because of a great projected demand for use as a polymer feedstock, particularly for use in producing degradable plastics. It is also used in the pharmaceutical and food industries, in leather tanning and textile dyeing, and in making solvents, inks, and lacquers. Although lactic acid can be prepared by chemical synthesis, production of lactic acid by fermentation of starch, cane sugar, whey or certain other carbon sources is a less expensive method. The production of lactic acid by fermentation is most efficient at a pH range where the lactic acid is largely present as a salt. Thus recovery of pure lactic acid often requires conversion of the salt into free acid and additional purification steps. One method that is used in purification is the production of a lactate ester from the lactic acid or salt, followed by purification of the ester. Finally the ester is converted to the free acid.

Lactic acid or other hydroxyacids or diacids can be converted to polyesters. These polyesters can be recycled via digestion using pressurized water, acid, base, or a combination of such treatments. The products of such digestion can be a mixture of organic acids, salts of organic acids, amides of organic acids. This digested recycled material can contain significant impurities and require purification to recover the organic acids or amides therein.

Additionally, during processing of ammonium salts of lactic acid, there is a tendency for lactamide to form via the following reaction

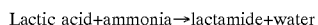

Lactic acid+ammonia→lactamide+water

Such organic acid amides can be formed in fermentation broths. Amides are typically purified by distillation or crystallization. Hydroxyamides, such as lactamide, can have relatively high boiling points and can be difficult to distill. Thus, there is a need for a better process to purify amides, in particular, hydroxyamides and other substituted amides.

There is a long standing need for improved processes for the production and recovery of relatively pure organic acids and organic acid amides, particularly lactic acid and lactamide.

SUMMARY OF THE INVENTION

The present invention is directed to an azeotropic distillation process for the recovery of an organic acid from a feed stream comprising the organic acid. The organic acid has from 2 to 8 carbon atoms, and can be a mono-, di- or tri-carboxylic acid. Preferably, the organic acid is a hydroxy acid, more preferably it is lactic acid.

The process can also be used to recover an organic acid amide from a feed stream containing organic acid amide. The organic acid of the amide has from 2 to 8 carbon atoms, and can be a mono-, di- or tri-carboxylic acid. Preferably, the organic acid of the amide is a hydroxy acid, more preferably the organic acid amide is lactamide. Alternatively, both an organic acid and an organic acid amide can be recovered from a freed stream comprising both.

The feed stream can comprise a fermentation broth that is unpurified or partially purified. The fermentation broth can be acidified and/or concentrated before being used as a feed stream. Alternatively, the feed stream can comprise an impure organic acid stream and/or an organic acid amide derived from sources other than fermentation, or a mixture thereof. In certain embodiments, the feed stream can comprise a digested polyester and the products of the digested polyester can be organic acids, salts of organic acids, or organic acid amides. Alternatively, the feed stream can comprise amides produced by reaction of (a) organic acids with ammonia, or (b) organic acid esters with ammonia, or by heating of organic acid ammonia salts.

The process can be used in either a batch or a continuous mode. In either mode, a feed stream that comprises the organic acid, and/or an organic acid amide is mixed with at least one azeotroping agent. The azeotroping agent preferably is a hydrocarbon capable of forming at least one first heteroazeotrope that comprises the azeotroping agent and the organic acid or the organic acid amide. In certain cases the first heteroazeotrope can further comprise water. In other cases, the azeotroping agent can be capable of forming a second heteroazeotrope consisting essentially of water and the azeotroping agent.

The feed stream is mixed with the azeotroping agent, and at least one of the feed stream, the azeotroping agent, or the mixture of the two is heated to produce a first vapor stream from the mixture. The first vapor stream comprises at least one first heteroazeotrope that comprises the organic acid or organic acid amide and the azeotroping agent. The first vapor stream is removed producing a first bottoms stream. The first bottoms stream can be present as two phases, it can separate into two phases upon cooling, or it can exist as a single phase. Preferably, this occurs while vacuum is being applied to the system. The first vapor stream can be condensed into a first liquid stream. The first liquid stream is capable of being separated into a first phase and a second phase. The first phase comprises the highest concentration of the organic acid and/or organic acid amide and the second phase comprises the azeotroping agent. The first vapor stream or the first liquid stream can undergo further distillation.

The first liquid stream can be separated into the first phase and the second phase, permitting the separation of the first phase from the remainder of the first liquid stream, resulting in recovery of the organic acid and/or organic acid amide. The recovered organic acid and/or organic acid amide in the first phase can then be further purified and/or concentrated. Preferably the recovered organic acid and/or organic acid amide has a lower concentration of impurities than the feed stream. When the recovered species is an organic acid, it is also preferred that the recovered organic acid is heat stable. Furthermore, it is preferred that the recovered organic acid or organic acid amide has a high degree of optical purity, preferably at least about 98% optical purity.

In certain embodiments, the first vapor stream can be condensed to form a first liquid stream that comprises a first phase having at least about 30 wt % water, and wherein the azeotroping agent is capable of forming a second heteroazeotrope consisting of water and the azeotroping agent, the process can further comprise either further heating and distilling of the first vapor stream or further heating, mixing and optionally distilling the first liquid stream, in either case producing a second vapor stream and a second bottoms stream, and removing the second vapor stream from the first liquid stream, producing the second bottoms stream. The second vapor stream comprises a second heteroazeotrope, as described above. The second vapor stream can be condensed to form two phases, fifth and sixth phases, one of which will be primarily water and the other primarily azeotroping agent. The bottoms liquid that remains after removal of the second vapor stream can be separated into a third phase and a fourth phase, wherein the third phase comprises a higher concentration of the organic acid and/or organic acid amide than the fourth phase. The fourth phase comprises the azeotroping agent. The organic acid and/or organic acid amide can be recovered by separation and removal of the third phase from the fourth phase and optionally purifying and/or concentrating the third phase. Preferably the recovered organic acid is heat stable. Preferably the recovered organic acid or organic acid amide also has a high degree of optical purity, more preferably greater than about 98% optical purity. It is also preferred that the recovered organic acid and/or organic acid amide has a lower concentration of impurities than was present in the feed stream.

There are at least two specific embodiments of the general process described above. Certain embodiments of the present invention can be run in a "wet" mode (e.g. the feed stream comprises at least about 10 wt % water, more preferably at least about 30 wt % water). Distillations or sequences of distillations that are run in the "wet" mode can, in some cases, involve more than one heteroazeotrope, wherein a first heteroazeotrope comprises the azeotroping agent and the organic acid or the organic acid amide and a second heteroazeotrope consists essentially of the azeotroping agent and water.

The first embodiment involves a "wet" feed stream comprising an organic acid and/or an organic acid amide, one or more salts of an organic acid (ammonium or other type salts), and more than about 10 wt % water. Heating of at least one of the feed stream, the azeotroping agent, or a mixture of the two results in the organic acid and/or amide undergoing azeotropic distillation, separating it from salts that are not distilled (e.g. vaporized intact). The first liquid stream from this "wet" mode can undergo further distillation(s) to purify and/or concentrate the organic acid and/or the organic acid amide. For example, if the azeotroping agent used in this first embodiment is capable of forming a second heteroazeotrope (e.g. consisting essentially of the azeotroping agent and water), further distillation can result in the purification or concentration or both of the organic acid and/or the organic acid amide that remains in liquid stream as the second heteroazeotrope is distilled off.

The second embodiment uses a feed stream that can be "dry" or "wet" and that comprises the organic acid and/or the organic acid amide, less than about 5 wt % salts and one or more impurities. This second embodiment relies on azeotropic distillation to remove the organic acid and/or the organic acid amide and to separate it from some or all of the impurities. Separation from impurities can be accomplished (1) when the impurities are not as readily distilled as the first heteroazeotrope and thus primarily remain behind in the first bottoms stream, and/or (2) when the impurities are distilled off. Impurities that are distilled off can have a lower boiling point than the first heteroazeotrope and they can thus be condensed, collected, and removed prior to the first heteroazeotrope being distilled off. Alternatively, the first heteroazeotrope and certain impurities can be distilled off and condensed together, and the resulting condensate (e.g. first liquid stream) can undergo further distillation to remove impurities and to recover purified and/or concentrated organic acid. Such impurities can be amino acids, other organic acids (e.g. pyruvic acid, acetic acid, and formic acid, among others), salts of organic acids (e.g. sodium salts), inorganic salts, alcohols (e.g. glycerol and 2,3-butanediol), proteins and carbohydrates (e.g. unfermented sugars).

Whether it is preferable to use a "wet" or a "dry" mode of the present invention can be determined by the nature of the feed stream, and in certain embodiments one or the other mode can be used exclusively for distillation(s) used in recovering organic acids. Both "dry" and "wet" modes can be used one after the other (in either order) in a single embodiment of the present invention. Furthermore a single embodiment of the present invention can be run in the "wet" mode wherein during the course of the azeotropic distillation process the "wetness" is increased.

Embodiments of the present invention can involve different types of contacting modes for mixing feed streams (e.g., azeotroping agent and lactic acid feed stream). The feed streams can both be liquids, or one feed stream can be a liquid, while the other is a vapor.

Other embodiments involve introduction of additional water as a liquid or vapor stream. The purposes for introducing additional water include: suppressing formation of lactic acid dimers and oligomers; aiding in the formation of more than one liquid phase; formation of different azeotropes for improved separation of components; reducing operating temperature of the system; washing lactic acid or impurities from one or more of the liquid streams; or for more than one of these purposes. There are various methods of mixing or introducing said additional water vapor or liquid that are known in the art.

In a batch mode, it is possible to distill off impurities that are more volatile prior to distillation of the organic acid heteroazeotrope or alternatively, when the impurities are less volatile than the first heteroazeotrope, the impurities can remain behind, as the organic acid is azeotropically distilled off. In certain embodiments, distillation can begin in the "dry" mode and can be switched to the "wet" mode during the course of the distillation by addition of water, or a distillation begun in the "wet" mode can be switched to a "wetter" mode during the course of the distillation, or begun in wet mode and switched to a dry mode later in the distillation. Alternatively, instead of batch, a continuous mode can be employed with two distillation columns in series, with light impurities being removed in one column and heavy impurities in a second column.

Certain impurities are expected to form their own azeotropes with the azeotroping agent, and the separation thus becomes a separation of one azeotrope from another. For example, pyruvic acid can be an impurity present in a lactic acid feed stream. If the azeotroping agent forms an azeotrope with pyruvic acid and another azeotrope with the organic acid being purified, and the two azeotropes have different boiling points (e.g., the pyruvic acid azeotrope has a lower boiling point than that of the organic acid azeotrope), the pyruvic acid can be removed from the organic acid via azeotropic distillation of the pyruvic acid azeotrope. Specifically a pyruvic acid/dodecane azeotrope can be distilled overhead, while a lactic acid/dodecane azeotrope with a higher boiling point remains behind as a bottoms distilling stream.

Thus the present invention can increase the recovery and purity of organic acid from impure feed streams.

DESCRIPTION OF ILLUSTRATIVE EMBODIMENTS

Figure 1:
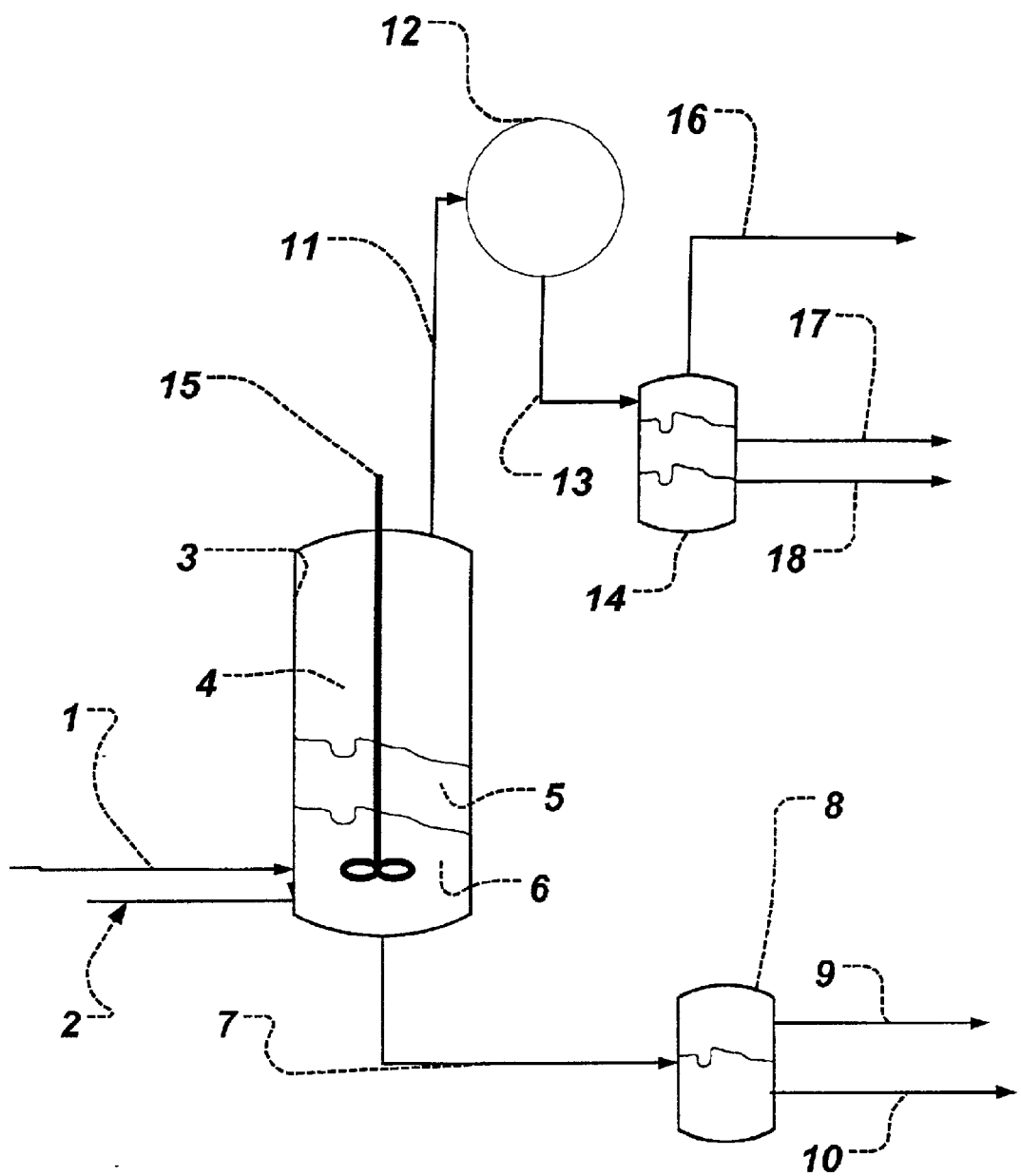
FIG. 1 is a process flow diagram in accordance with certain processes of the present invention for recovery of an organic acid.

The following definitions are used in this patent. "Lactic acid" refers to the monomeric free lactic acid as is commonly found is dilute aqueous solutions. "88% lactic acid" and "lactic acid of commerce" refer to a typical commercially available lactic acid, which is actually a mixture of monomeric lactic acid, linear dimer lactic acid or lactoyl lactic acid, short chain lactic acid oligomers, water, and also a small quantity of cyclic dimer lactic acid or lactide. When this lactic acid is diluted in a large excess of water, it will slowly hydrolyze or convert to all monomeric form lactic acid. When concentrated lactic acid is diluted with water to a 50 wt % concentration, it will slowly hydrolyze to a mixture that is largely monomeric lactic acid, but which can still contain about 3 to 4 wt % dimer lactic acid, and trace amounts of higher oligomers.

"Organic acid amide" is defined here as an amide derived from reaction of ammonia with an organic acid. It is the preferred that the organic acid amide is not a secondary or tertiary amide produced by the reaction of one or two amine compounds with an organic acid. Organic acid amides herein can be species such as acetamide or lactamide or other amides. Note that lactamide can be present as optically pure L-lactamide, optically pure D-lactamide, or a mixture containing varying proportions of the D and L isomers.

"Distillation" is defined here to mean either multistage distillation or rectification, either continuous or batch wise, as well as single stage distillation and condensation, continuous or batch wise. Multistage distillation can involve the use of reflux to increase the purity of the overhead stream and use of a reboiler or introduction of hot vapors to the bottom of the column to increase the purity of the bottoms stream, as distinguished from a single stage distillation or simple evaporation.

"Azeotrope" and "azeotropic" are used herein to refer to systems that contain true azeotropic mixtures as well as those that are substantially azeotropic in nature (e.g., wherein the weight percentage of each component in the mixture in the liquid phase differs from the weight percentage of that same component in the vapor phase by no more than about 5 wt %, preferably by no more than about 2 wt %, more preferably by no more than about 1 wt %).

A "heteroazeotrope" is an azeotrope that comprises more than one liquid phase.

A "binary heteroazeotrope" is an azeotrope that comprises more than one liquid phase and involves primarily two species of chemical compounds.

A "ternary heteroazeotrope" is an azeotrope that comprises more than one liquid phase and involves primarily three chemical species.

The "optical purity" of an α-hydroxyacid is defined as the molar ratio of one optical isomer to the total level of both isomers. For species that form oligomers and short and long chain polymers, the optical purity can be measured and expressed on a basis after the oligomers and polymers have been converted to monomers.

A "racemic lactic acid mixture" is defined as an equal mixture of D and L lactic acid optical isomers. An organic acid recovered using methods of the present invention is deemed "heat stable" if a sample of the separated first phase (or third phase, in certain embodiments), as defined above, can be concentrated (e.g. less than 5 wt % water) by heating at a temperature of up to about 140° C., and then heating the concentrate to 180° C. and holding it at 180° C. for two hours without color forming. Color formation under these conditions occurs when certain impurities are present, particularly when certain impurities often found in fermentation broths are present.

"Diethylbenzene" herein refers to either mixed isomers (1,4-diethylbenzene, 1,3-diethylbenzene, and 1,2-diethylbenzene) or a single pure diethylbenzene isomer.

Production of an organic acid such as lactic acid by fermentation is well known. A person skilled in the art will be familiar with reactants, equipment, and process conditions suitable for such fermentation. The result of the fermentation will be an aqueous broth that comprises the acid, salts of the organic acid, in addition to other organic salts, inorganic salts, protein fragments, sugar residues, other organic acids, alcohols, ketones, and metal ions. Preferably, the feed stream of the present invention comprises a fermentation broth. The broth can be partially purified, for example by filtration or centrifugation, to remove some of the impurities. At least about 75 wt % of the whole cells and cellular debris has been removed in a partially purified fermentation broth. In certain embodiments it is preferred that the broth also be concentrated. Furthermore the fermentation broth can also be acidified prior to being used as a feed stream in the present invention. Furthermore the fermentation broth can also be de-cationized, that is, alkali and alkaline monovalent, divalent and trivalent cations are to a large extent removed and replaced with the hydronium (H+) ion prior to being used as a feed stream in the present invention. Preferably all the alkali and alkaline monovalent, divalent and trivalent cations are exchanged. This cation exchange is performed using a solid or liquid ion exchanger primarily in the hydrogen form. One example of such a solid ion exchange resin is the Amberlite IR-120H+ resin (Rohm and Haas).

Furthermore, the broth can be partially purified in one or several other ways known in the art before treatment in this process. Furthermore, the broth can be additionally purified or concentrated further after treatment by this invention.

The feed stream can comprise amides produced by reaction of (a) organic acids with ammonia or (b) organic acid esters with ammonia, or by heating of organic acid ammonium salts. Formation of amides from organic acids in the presence of ammonia is well known in the art. For example, a fermentation broth comprising an ammonium salt of an organic acid can be thermally treated resulting in the formation of amides of the organic acid, and the thermally treated fermentation broth can be used as a feed stream in the present invention. Preferably when the feed stream comprises an organic acid amide, the organic acid amide is an amide of a hydroxy acid, more preferably it is lactamide.

Certain embodiments of the present invention can be better understood by reference to FIG. 1. In an embodiment of the present invention run in the batch mode, a batch charge of feed stream 1 is made to reactor 3. The feed stream 1 comprises an organic acid and/or an organic acid amide to be recovered. The organic acid to be recovered is selected from the group consisting of organic acids having from 2 to 8 carbon atoms and is a monocarboxylic, dicarboxylic or tricarboxylic acid. Preferably the organic acid is a hydroxy organic acid that has from 2 to 8 carbon atoms. Furthermore, the hydroxy organic acid can be an alpha, beta, delta, gamma, or epsilon hydroxy acid. The organic acid can be selected from the group consisting of lactic acid, pyruvic acid, beta-hydroxybutyric acid, hydroxyacetic acid, glycolic acid, propionic acid, and acetic acid, among others. Preferably the organic acid is a hydroxy acid, more preferably the organic acid is lactic acid. It is preferred that the organic acid that is recovered using processes of the present invention is heat stable, more preferably the recovered organic acid is a heat stable lactic acid. In certain embodiments, it is preferred that the recovered organic acid is an alpha hydroxy acid that is at least about 98% optically pure. The ammonium salts that are present in feed streams of certain embodiments are ammonium salts of the organic acids described above. The organic acid amide that is recovered from the feed stream in certain embodiments is selected from the group consisting of amides of monocarboxylic acids, dicarboxylic acids, and tricarboxylic acids having from 2 to 8 carbon atoms. Preferred organic acid amides include lactamide, pyruvamide, beta-hydroxy butyamide, propionamide, and acetamide, among others. In certain embodiments, both a organic acid and an organic acid amide are recovered as described above.

A batch charge comprising at least one azeotroping agent 2 is also made to the reactor 3. Azeotroping agents used in methods of the present invention are selected so that they are capable of forming at least one first heteroazeotrope that comprises the azeotroping agent and the organic acid or the organic acid amide that is to be recovered from the feed stream 1. Embodiments of the present invention can involve (i) a single first heteroazeotrope that is binary (e.g. consisting essentially of the organic acid or the organic acid amide and the azeotroping agent 2), (ii) a single first heteroazeotrope that is ternary (e.g. consisting essentially of the organic acid or organic acid amide, water, and the azeotroping agent), or (iii) more than one first heteroazeotrope (e.g. one that is binary and another that is ternary, or alternatively, one heteroazeotrope comprising the organic acid and a different heteroazeotrope comprising the organic acid amide). In certain embodiments, the azeotroping agent can be capable of forming a second heteroazeotrope comprising water that does not comprise the organic acid. If essentially no other chemical species are part of the second heteroazeotrope, it can be a binary heteroazeotrope.

Preferably, the at least one azeotroping agent is a hydrocarbon having a boiling point of between about 100° C. less than and 150° C. more than the boiling point of the organic acid that is being recovered (e.g. the boiling points as compared at the same pressure). More preferably, the azeotroping agent has a boiling point of between about 50° C. less than and 50° C. more than the organic acid boiling point. If the azeotroping agent has a boiling point lower than that of the organic acid (at the same pressure), then the distillation can be operated under relatively cooler conditions, however the first vapor stream 11 will tend to be less rich in organic acid than if an azeotroping agent having a boiling point higher than that of the organic acid is used. If the azeotroping agent boils at a temperature above that of the organic acid, then the heteroazeotrope can have a relatively higher boiling point and the first vapor stream 11 can be richer in the organic acid. However, a higher boiling point first heteroazeotrope can lead to a process with more unwanted side reactions in certain cases, or in other cases, can lead to desirable reactions (e.g. the formation of lactide).

The azeotroping agent can in certain embodiments be a hydrocarbon having 7 to 16 carbon atoms, especially those embodiments involved in the recovery of lactic acid. Hydrocarbons used as azeotroping agents can be either aromatic or aliphatic, and aliphatic hydrocarbons can be branched, unbranched or cyclic. The azeotroping agent can in certain embodiments be an aliphatic hydrocarbon having 10 to 16 carbon atoms, especially those embodiments involved in the recovery of lactic acid. The azeotroping agent can in certain embodiments be an aromatic hydrocarbon having 9 to 15 carbon atoms, especially those embodiments involved in the recovery of lactic acid. The azeotroping agent can be, in certain embodiments, an ether, for example an ether having from 7 to 16 carbon atoms. Ethers used as azeotroping agents can be either aliphatic or aromatic. Examples of ethers that can be used as azeotroping agents in certain embodiments (especially those for the recovery of lactic acid) include dimethylene glycol dimethyl ether and dipropylene glycol dimethyl ether, among others. The azeotroping agent can in certain embodiments be a long chain alcohol having 7 to 13 carbon atoms, especially those embodiments involved in the recovery of lactic acid. Examples of hydrocarbons suitable for use as azeotroping agents in certain embodiments (especially those for the recovery of lactic acid) include diethylbenzene, hexadecane, tetradecane, dodecane, decane, octylbenzene, and propylbenzene, among others. Certain solvents, such as p-xylene and toluene, which are commonly discussed in the literature relating to solvent processing of lactic acid to form lactide, appear not to form azeotropes with lactic acid and appear not to be suitable for azeotropic distillation of lactic acid. Preferably the azeotroping agent used in recovering lactic acid is diethylbenzene, octylbenzene or dodecane, more preferably dodecane.

In certain embodiments, more than one azeotroping agent can be used, for example benzene and cyclohexane can be used as azeotroping agents with a fluid stream comprising acetic acid and water. Acetic acid, benzene, and cyclohexane form a ternary azeotrope, and acetic acid and benzene form a binary azeotrope. Both the binary and ternary azeotropes are heteroazeotropes and can be used in an embodiment of the present invention to recover acetic acid through an azeotropic distillation in which acetic acid is recovered from an aqueous phase 18 (e.g. the first phase described above) that has been separated from the azeotroping agents 17 (e.g. the second phase described above).

The two batch charges 1 (e.g. feed stream) and 2 (e.g. azeotroping agent) are not fully miscible and two liquid phases 5 and 6 are observed. A stir bar 15 is added to the reactor 3 and stirred at sufficient speed to create a turbulent interface and some dispersion of droplets of phase 6 into phase 5. This causes a vortex, but does not completely mix the two phases. There are several possible alternatives for mixing (e.g. contacting) the azeotroping agent 2 and the feed stream 1 in the present invention. For example, the azeotroping agent that is mixed with the feed stream can be in the form of a vapor. When the azeotroping agent 2 is introduced as a vapor, the azeotroping agent and the feed stream can be mixed with one another in a column or they can be mixed with one another in a flash reactor. The mixing can, for example, be done in a tray distillation column, a random packed column, or a structured packed column. Furthermore, the mixing of the azeotroping agent and the feed stream can be done in a countercurrent fashion.

Heat is applied to reactor 3 and a first vapor stream 11 comprising the first heteroazeotrope (e.g. comprising azeotroping agent and organic acid or organic acid amide) travels from the reactor headspace 4 to condenser 12. Alternatively, heat can be applied to at least one of the feed stream 1, the azeotroping agent 2, or the mixture of the two 5, 6. Furthermore, in certain embodiments the first vapor stream 11 can comprise both organic acid and organic acid amide, so that both are removed from impurities present in the feed stream 1 that are not vaporized. When both organic acid and organic acid amide are being recovered via the first vapor stream 11, it is preferred that the organic acid is lactic acid and the organic acid amide is lactamide and that the azeotroping agent 2 is a linear or branched alkane with a normal boiling point of between about 150° C. and 270° C. In certain embodiments a vacuum can be applied to aid in the removal of the vapors from the reactor headspace 4.

The preferred temperature range in the reactor 3 is related to the boiling points of the azeotroping agent, the organic acid and/or organic acid amide, the first heteroazeotrope, and impurities, as well as the system pressure and the concentrations of organic acid and/or amide and water in the feed stream (e.g. whether it is being run in the "wet" or "dry" mode). The preferred temperature range for the mixture in the present invention is between about 50° C. and 200° C. This temperature range can be achieved by heating at least one of the feed stream, the azeotroping agent, or the mixture of the two. As an example, when using dodecane as an azeotroping agent with a feed stream comprising 50 wt % lactic acid and a system pressure of −22.4 mm Hg, the temperature is preferably between about 110° C. to 145° C. Other factors affecting the selection of an appropriate system temperature within such a range are known in the art. For example, whether the process is being run in batch or continuous mode can influence the choice of appropriate system temperatures. If run in the continuous mode the type of equipment used in the process can be a further consideration (e.g. whether a stripper column or a continuous stirred tank reactor (CSTR) is used). Heating of the reaction can be accomplished using methods known in the art, and as pointed out above the heating is performed on at least one of the feed stream, the azeotroping agent, or the mixture of the two. The system pressure is typically held constant. Relatively wetter feeds can be run at cooler temperatures. In certain embodiments it is preferred that the process is carried out at about atmospheric pressure (e.g., about 12.7 to 16.7 psia).

In cases in which the azeotroping agent boils at a temperature above that of the organic acid or organic acid amide, the first heteroazeotrope (comprising the organic acid or organic acid amide and the azeotroping agent) typically has a hotter boiling point and the first vapor stream 11 is relatively richer in organic acid and/or organic acid amide. The higher temperature required to vaporize the first heteroazeotrope can lead to more unwanted side reactions in certain cases. Alternatively, in other cases the relatively high temperature used for azeotropic distillation of the organic acid and/or organic acid amide can lead to formation of desirable products (e.g. lactide which can be incorporated into other industrial processes).

The condensate 13 (e.g. first liquid stream) enters into receiver 14, where it can be separated into phases 17 (e.g. second phase) and 18 (e.g. first phase). Samples of the first phase 18 and of the second phase 17 can be periodically removed after separation of the two phases. The organic acid and/or the organic acid amide is recovered in the first phase 18. Generally, the second phase 17 will comprise the azeotroping agent(s). When the azeotroping agent has a lower density than the first phase that comprises the recovered organic acid and/or the organic acid amide, it forms the upper phase of the first liquid stream 13 from the first vapor stream 11. Diethylbenzene or dodecane is used as the azeotroping agent in examples below, and in these examples, these compounds have a lower density than the first phase (phase comprising the recovered organic acid). After the first vapor stream 11 is removed and condensed to a first liquid stream 13, the diethylbenzene or dodecane can separate on top of the first phase 18, and is therefore referred to as the light phase in the examples that follow. The first phase 18 is referred to as the heavy phase in the examples. However, relative positions of the first phase 18 and second phase 17 can vary depending on their relative densities.

There are two temperature probes in the vapor space 4, one located above the reactor liquid 5 and 6 and another in the vapor space at the system head prior to the condenser 12. Bottoms residue stream 7 can be removed from reactor 3 to a receiver 8. The first bottoms stream 7 can be separated into phases 9 and 10 in the receiver 8. Phase 9 generally comprises the azeotroping agent, while phase 10 comprises the heavy phase (e.g. comprising organic acid) bottoms.

The organic acid is recovered when the first phase 18 is separated and removed. Preferably the recovered organic acid has a lower concentration of impurities than the feed stream. It is also preferred that the recovered organic acid is heat stable, and in certain embodiments the organic acid is preferably an alpha hydroxy acid that is optically pure. After separation and removal of the first phase 18 from the second phase 17, the recovered organic acid can be further purified and/or concentrated. Residual azeotroping agent present in the first phase 18 can be stripped from it, or the separated first phase 18 can be subjected to further distillation operations to separate various impurities or azeotropes that it comprises.

Separation and removal of the azeotroping agent from liquid streams comprising heteroazeotropes can be conducted using systems known in the art for purifying a heterogeneous azeotrope comprising an aqueous phase and an azeotroping agent. For example, when separating the two phases of a first liquid stream, two columns can be used that are both served by a common liquid-liquid decanter. The bottoms from one column after distillation can be purified organic acid and/or organic acid amide, while the bottoms from the other column can be purified azeotroping agent. When recovering reactive organic acids, such as hydroxyacids, such a system can optionally be run at reduced pressure (e.g. between about 1 and 10 psia) to avoid or reduce the formation of oligomers. The contacting mode can be such that residence times are limited to reduce the extent of oligomer formation. Optionally, water can be introduced at certain points in the process to suppress formation of oligomers. Subsequently, and optionally, water can be stripped from recovered azeotroping agent or recovered organic acid or organic acid amide using a water strip agent or other method as part of the recovery process.

If the azeotroping agent boils below the boiling point of the organic acid or organic acid amide, then the azeotroping agent can be readily separated from the phase comprising the recovered organic acid or amide by using stripping type distillation that is known in the art.

In some instances the first phase 18 with recovered organic acid and/or organic acid amide can be integrated into another industrial process. For example a separated first phase 18 with recovered lactic acid that resulted from an azeotropic distillation with diethylbenzene as the azeotroping agent provides a feed for other processing steps as described in the co-filed application, "Azeotrope Distillation of Cyclic Esters of Hydroxy Organic Acids". Thus, in certain embodiments, the separated and removed first phase may not need to be stripped of residual azeotroping agent or of certain other compounds, if they either do not interfere with downstream processing or actually provide a benefit to subsequent processes.

As an alternative to the batch method described above, the process can be run in the continuous mode, wherein there can be a continuous feed of feed stream 1 into reactor 3 and a continuous feed of azeotroping agent 2 into reactor 3. Furthermore the azeotroping agent from phases 9 and/or 17 can in certain embodiments (run either in batch or continuous mode) be recycled for use in a continuous process or in subsequent batch or continuous processes of the present invention. Still further, in certain embodiments, phase 10 (e.g. the phase of the first bottoms stream comprising the organic acid and/or the organic acid amide) can also be recycled as part of the feed stream 1 for a continuous process or for subsequent batch or continuous processes.

The present invention provides means for recovering organic acid and/or organic acid amide from a fermentation broth. However, it should be understood that the present invention is not limited to use in conjunction with fermentation, nor is it limited to use with broth that has been purified, acidified, and/or concentrated, as pointed out above. For example, phase 10 of the bottoms (the undistilled liquid in the reactor 3 after removal of first heteroazeotrope) can be used in a feed stream. Preferably, phase 10 (comprising organic acid and/or organic acid amide that failed to be azeotropically distilled off) of the first bottoms stream used as feed stream is the result of a previous batch mode azeotropic distillation of the organic acid and/or amide. In certain embodiments when the phase of the first bottoms stream comprising remaining organic acid and/or amide is used as a feed stream it is preferred that water be added to the feed stream, as well. The phase of the first bottoms stream comprising organic acid and/or amide remaining after azeotropic distillation tends to comprise dimeric, trimeric, and linear polymeric organic acid (e.g. polylactic acid) and the addition and mixing in of water can permit hydrolysis of such components to produce monomeric organic acid that can be further recovered by azeotropic distillation, thus leading to higher process yields. Thus in certain embodiments, water is continuously fed subsurface to a reaction mixture of bottoms (e.g. feed stream) and of an azeotroping agent. In other instances, the feed stream can be derived from other sources. The feed stream used in the present invention comprises a stream of an organic acid or an organic acid amide, or both. The feed stream can further comprise water and/or impurities, including salts of organic acids, as described above.

Additionally, the invention can be used to recover organic acid from recycled polylactide polymer, polylactic acid polymer, or polyesters containing substantial portions of lactic acid or other hydroxy acids. For example, a crude shredded polymer can be treated with a heated aqueous phase to hydrolyze some or all of the polymer and the resultant stream can then be used as a feed stream to one of the embodiments of this invention. Alternatively, said polymer can be treated with an ammonia containing stream that will act to increase the rate and extent of hydrolysis of the polymer prior to or simultaneously with one of the azeotropic distillation embodiments presented here.

Additionally, the invention can be run in equipment and using methods such that the rate and extent of racemization is limited. This can be done by limiting the amount of time that the mixture of azeotroping agent and feed stream is exposed to high temperatures (e.g. temperatures that favor racemization reactions). For example, by the using a vapor-liquid contactor the contact time can be decreased. Selection of devices such as wiped film evaporators, nitrogen swept reactors or columns, and low holdup packed distillation systems, as well as selection of conditions that limit temperature and time contact such as using reduced pressure are well known in the art.

As stated above, methods of the present invention can be run in a continuous mode or in a batch mode. When run in continuous mode the feed stream 1 and the at least one azeotroping agent 2 are introduced as continuous feeds. In certain embodiments in which the method is practiced in a continuous mode, it is preferred that a periodic or small, continuous purge of heavy impurities in the first bottoms stream of the reaction chamber be performed. Reflux steps can be used in methods of the present invention, but are not required.

As described above, the present invention has at least two different, significant embodiments. The first embodiment involves a "wet" feed stream comprising an organic acid and/or an organic acid amide, one or more salts of an organic acid and water. When an organic acid is to be recovered using this embodiment, the salt or salts can be salts of the organic acid that is recovered. The salts of an organic acid present in the feed stream can be ammonium or other salts, like sodium, calcium, or potassium salts of the organic acid. Preferably the feed stream for the first embodiment of embodiments comprises between about 15 wt % to 85 wt % the organic acid or the organic acid amide that is to be recovered, and greater than about 10 wt % water, and between about 5 wt % and 70 wt % at least one salt of an organic acid. When an organic acid is being recovered the at least one salt can be a salt of the organic acid that is recovered. Heating in methods of this embodiment results in the organic acid and/or organic acid amide undergoing azeotropic distillation, separating it from a salt or salts, which undergo essentially no thermal decomposition.

The first phase of the first vapor stream of this embodiment can undergo further distillation to remove water or impurities, if present. That is, the condensate of the vaporized organic acid heteroazeotrope (e.g. first heteroazeotrope) can be readily subjected to further purification by distillation. In one example of this embodiment, a typical feed stream can be a fermentation broth or concentrated fermentation broth that has a pH near the pKa of the organic acid to be recovered. Under these conditions, about half of the moles of organic acid moiety are present as free acid which can be azeotropically distilled, and the other about half is present as salts of the organic acid. After azeotropic distillation, the free acid is recovered overhead and the residue left behind can be recycled as a buffer material for subsequent fermentations.

The second embodiment involves a feed stream that comprises an organic acid and/or organic acid amide, little or no salts and one or more impurities. This embodiment permits the removal of the organic acid and/or the amide from the impure feed stream and can result in a certain amount of its impurities that are not as readily distilled being left behind in the first bottoms stream and/or certain impurities can be distilled off in early fractions of vapor phase condensate and removed prior to azeotropic recovery of the organic acid. Impurities that can be present include amino acids, other organic acids (e.g. pyruvic acid), salts of organic acids (e.g. sodium salts), amides, alcohols (e.g. glycerol and 2,3-butanediol), and carbohydrates (e.g. unfermented sugars). Impurities such as lactamide and pyruvic acid can be preferentially distilled overhead away from organic acid, like lactic acid, in certain cases of this second embodiment, when it is operated in a batch mode with a wet feed. Fractions collected from the condensate of the vapor stream removed early in the recovery process, are rich in water and lactamide and pyruvic acid with little or no organic acid. Fractions of the first phase collected later in the recovery process comprise relatively high levels of organic acid with a smaller percentage of these impurities.

Alternatively, the process can be used to purify organic amide species produced by reaction of organic acids or via other means. For example, an aqueous feed stream rich in lactamide can be purified via azeotropic distillation.

Preferably the feed stream for this last embodiment comprises greater than about 15 wt % the organic acid and/or organic acid amide, less than about 5 wt % salts, and at least one impurity, as described above. The salts can be salts of an organic acid to be recovered, other organic salts, or inorganic salts. The feed stream for this embodiment can be either "dry" (having less than about 10 wt % water) or "wet" (having greater than about 10 wt % water). In certain cases this embodiment can involve a feed stream that initially comprises up to about 30 wt % water, and during the course of the process involving azeotropic distillation water is added to the feed stream in an amount that is sufficient to shift the volatility of at least one impurity in the feed stream. The amount of added water sufficient to shift the volatility can alter the composition of the feed stream such that it comprises at least about 50 wt % water. The water can be added after mixing the feed stream and the azeotroping agent and prior to heating the mixture, or the water can be added during heating of the mixture to produce the first vapor stream. The concentration of the impurity in the first liquid stream resulting from heating the mixture prior to addition of water differs from the concentration of the impurity in the first liquid stream after addition of the water.

Figure 2:
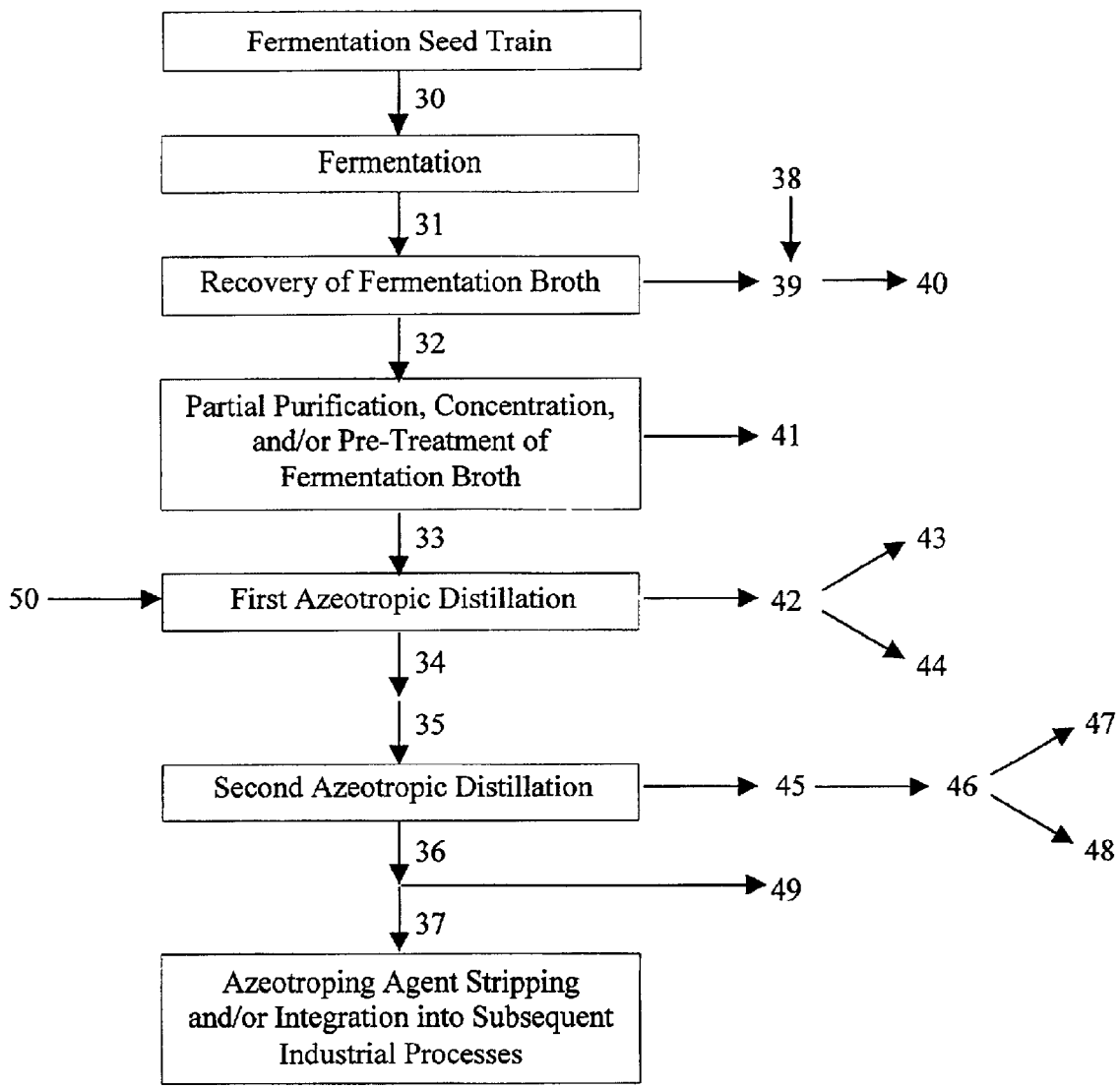
FIG. 2 is a flow diagram in accordance with certain processes of the present invention that comprise at least two azeotropic distillations.

As stated above, the first liquid stream recovered from a first azeotropic distillation of an organic acid and/or an organic acid amide can undergo additional distillation to increase purity and/or concentration of the organic acid and/or amide. A schematic of a process implementing further distillation is diagrammed in FIG. 2. A fermentation seed stock 30 is generated using a fermentation seed train. The fermentation seed stock 30 is introduced into the scaled up fermentation for the production of organic acid and/or organic acid amide, along with fresh nutrients, water, and a carbon source. Methods of fermentation are known in the art. After fermentation the cell culture 31 can comprise organic acid, cells, cellular debris, fermentation products, impurities (e.g. other organic acids and salts, among others), water, and unused carbon source. The cell culture 31 is then processed to recover the fermentation broth 32. Cells and cellular debris 39 can be removed by filtration or centrifugation. The fermentation broth 32 can then undergo partial purification and/or pre-treatment prior to a first azeotropic distillation. Partial purification can, for example, comprise precipitation and removal of certain impurities. A pre-treatment can comprise acidification to obtain more free organic acid in the fermentation broth. Preferably the fermentation broth is concentrated by removal of water and solvents 41 produced by fermentation. The concentrated, pre-treated fermentation broth 33 can comprise organic acid and/or organic acid amide and at least about 30 wt % water.

The concentrated, pre-treated fermentation broth 33 is mixed with an azeotroping agent 50 (e.g. diethylbenzene) and the mixture is heated to produce a first vapor stream 34 and a first bottoms stream 42, as part of the first azeotropic distillation. The first azeotropic distillation can involve a first column. The first vapor stream 34 comprises a first heteroazeotrope comprising organic acid or organic acid amide and the azeotroping agent and can further comprise water vapor. The first vapor stream 34 is condensed to a first liquid stream 35. The first liquid stream 35 can, in certain embodiments, comprise at least about 30 wt % water, organic acid and/or organic acid amide and the azeotroping agent.

In cases in which the azeotroping agent is capable of forming a binary second heteroazeotrope, consisting essentially of water and the azeotroping agent, the process can further comprise a second azeotropic distillation of the first liquid stream 35. The second azeotropic distillation can be performed using a second column, and involves heating and mixing the first liquid stream 35 to produce a second vapor stream 45 and a second bottoms stream 36. The second vapor stream 45 is separated from the first liquid stream 35, producing the second bottoms stream 36. The second vapor stream 45 comprises a second heteroazeotrope consisting essentially of water and the azeotroping agent. The second bottoms stream 36 that remains after removal of the second vapor stream 45 can be separated into a third phase 37 and a fourth phase 49. The third phase 37 comprises a higher concentration of the organic acid and/or amide than the fourth phase 49, and the fourth phase 49 comprises the azeotroping agent. The organic acid and/or amide can be recovered by separation and removal of the third phase 37 from the fourth phase 49.

The third phase can, optionally, be further purified and/or concentrated. For example residual azeotroping agent can be steam stripped from the third phase 37. Alternatively if components other than the organic acid or amide are present in the third phase that will not interfere with downstream processing, the entire third phase 37 can be used in subsequent industrial processes. Preferably the recovered organic acid and/or amide in the third phase 37 is heat stable, and in certain embodiments it is preferred the organic acid is an alpha hydroxy acid that at least about 98% optically pure. It is also preferred that the recovered organic acid and/or amide has a lower concentration of impurities than was present in the feed stream.

Thus, in certain processes of the present invention the feed stream 33 and the azeotroping agent 50 can undergo mixing in a first fractional distillation column where upon heating of at least one of the azeotroping agent 50, the feed stream 33, or the mixture of the two, a first vapor stream comprising a first azeotrope is produced. Preferably the azeotroping agent is a hydrocarbon that is capable of forming at least one azeotrope with organic acid or organic acid amide of the feed stream 33, and that is greater than about 99% free of other hydrocarbons. The first vapor stream 34 can be introduced as a vapor stream or condensed and introduced as a fluid into a second fractional distillation column that aids in separation of a second vapor stream 45 thereby producing a second bottoms stream 36 comprising the organic acid or the organic acid amide. By using a first fractional distillation column and a second fractional distillation column in series, the organic acid or organic acid amide produced can be substantially free of impurities. Preferably the product (e.g., the removed third phase) from such a serial distillation process has less than about 5 wt % impurities, more preferably less than about 1 wt % impurities, and most preferably less than about 0.1 wt % impurities.

The by-products of this double azeotropic distillation should be noted. First, regarding the cellular material 39 removed from the cell culture 31, water or aqueous media 38 can be added to cellular material 39 and washed cells 40 can be recovered. Depending on the nature of the washed cells and cellular material 40, they can be further processed as components in other processes or products.

Furthermore, the first bottoms stream 42 of the first azeotropic distillation can, optionally, be separated into two phases 43 and 44. Phase 43 comprises unused azeotroping agent and phase 44 can comprise undistilled organic acid and/or amide, along with certain impurities. Both phases can be recycled in subsequent azeotropic distillations. For example, water can be added to phase 44 to hydrolyze oligomers of organic acid and it can be re-used as a feed stream, and the azeotroping agent of phase 43 can also be recycled in subsequent azeotropic distillations. Likewise, the second vapor stream 45 of the second distillation comprising the second heteroazeotrope (consisting essentially of water and azeotroping agent) can be condensed to a second liquid stream 46 that can be separated into two phases 47 and 48. Phase 47 comprises azeotroping agent, and phase 48 comprises water. The azeotroping agent in phase 47 can be recycled for subsequent azeotropic distillation processes. Likewise, the fourth phase 49 comprising azeotroping agent can be recycled.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Recovery of Lactamide and Lactic Acid from a Feed Stream Comprising Lactic Acid and Four Impurities Using diethylbenzene as an Azeotroping Agent in a One Day Batch Process without Reflux A 250 ml three neck flask with a stirrer was charged with reagents. The system pressure was −25.6 inches Hg gauge. The overhead vapor was drawn to a condenser and condensate receiver. There was little or no reflux. The typical liquid temperature during the run was 108° C. The vapor immediately above the liquid was 104° C. The vapor at the top of the head prior to entering the condenser was 100° C.

The following table shows the initial pot charge amounts. This was a batch distillation, so there were no continuous feeds.

| Component | grams |
|---|---|
| 88% Lactic acid in water | 55.9 |
| Diethylbenzene | 81.2 |
| Glucose | 1.0 |
| Succinic acid | 1.0 |
| Glycine | 1.2 |
| Glycerol | 1.0 |
| Water | 7.1 |

Thirteen overhead condensate samples ("OV1" to "OV13") were collected. The samples consisted of a light phase (e.g. comprising the diethylbenzene, azeotroping agent) and a heavy phase. The heavy phase contained the recovered lactic acid. The phases were separated and samples from each phase were analyzed by HPLC. The undistilled residue left in the flask or first bottoms stream, "BTMS", was also analyzed. The thirteenth sample ("OV13") was not analyzed.

| OVERALL MASS BALANCE | | | | | | | | | | | | | | | |
|---|---|---|---|---|---|---|---|---|---|---|---|---|---|---|---|
| | Feed | OV1 | OV2 | OV3 | OV4 | OV5 | OV6 | OV7 | OV8 | OV9 | OV10 | OV11 | OV12 | OV13 | BTMS |
| Mass of light phase (grams) | 81.2 | — | 2.2 | 1.58 | 1.68 | 2.95 | 4.04 | 7.773 | — | — | 4.72 | — | — | — | 21.742 |
| Mass of heavy phase (grams) | 66.9 | — | 1.0 | 2.52 | 2.05 | 3.05 | 1.81 | 0.830 | — | — | 0.74 | — | — | — | 48.55 |
| Total mass (grams) | 148.1 | 3.6 | 3.2 | 4.10 | 3.73 | 6.09 | 5.85 | 8.603 | 6.35 | 3.44 | 5.46 | 6.62 | 12.83 | 1.77 | 70.29 |

| HEAVY PHASE COMPONENT CONCENTRATIONS (% w/w) | | | | | | | |
|---|---|---|---|---|---|---|---|
| | Feed | OV1 | OV2 | OV3 | OV4 | OV5 | OV6 |
| Lactic acid | 60.3 | 0.1 | 0.2 | 0.1 | 0.3 | 2.0 | 14.8 |
| Water | 29.3 | 99.9 | 99.8 | 99.9 | 99.7 | 97.8 | 84.9 |
| Lactamide | 0 | 0.018 | 0.020 | 0.020 | 0.040 | 0.075 | 0.096 |
| Pyruvic acid | 0.109 | 0.005 | 0.022 | 0.011 | 0.033 | 0.118 | 0.167 |
| | OV7 | OV8 | OV9 | OV10 | OV11 | OV12 | BTMS |
| Lactic acid | 16.4 | 26.0 | 27.1 | 27.0 | 26.7 | 34.1 | 20.8 |
| Water | 83.3 | 73.6 | 72.6 | 72.6 | 73.0 | 65.5 | 62.6 |
| Lactamide | 0.062 | 0.10 | 0.035 | 0.078 | 0.024 | 0.014 | 0 |
| Pyruvic acid | 0.187 | 0.138 | 0.149 | 0.162 | 0.045 | 0.017 | 0 | no reflux. The typical liquid temperature during the run rose from 120° C. to 138° C. The temperature of the vapor immediately above the liquid rose from 120° C. to 130° C. during the run. The vapor temperature at the top of the head prior to entering the condenser was 124° C.

Seven overhead condensate samples ("OV") were collected. The samples consisted of a light phase (comprising the azeotroping agent) and a heavy phase (comprising the recovered lactic acid). The phases were separated and samples collected from the first five heavy phases (e.g. comprising lactic acid) were analyzed by HPLC. The undistilled residue left in the flask, "BTMS", was also analyzed.

| OVERALL MASS BALANCE | | | | | | | | | |
|---|---|---|---|---|---|---|---|---|---|
| | Feed | OV1 | OV2 | OV3 | OV4 | OV5 | OV6 | OV7 | BTMS |
| Mass of light phase (g) | 50.0 | 1.87 | 3.834 | 8.76 | 8.92 | 7.623 | — | — | 8.999 |
| Mass of heavy phase (g) | 40.0 | 4.53 | 1.496 | 2.042 | 1.052 | 0.751 | — | — | 26.2 |
| Mass of both phases (g) | 90.0 | 6.4 | 5.33 | 10.802 | 9.972 | 8.374 | 9.098 | 2.721 | 35.199 |

In this example, water distills overhead in the early fractions and lactic acid is more concentrated in the later fractions. Ammonia was not added initially, but lactamide was produced in this distillation. Lactic acid reacted with glycine to form lactamide. Pyruvic acid is an oxidation product of lactic acid. This example also shows that pyruvic acid and lactamide can be separated from lactic acid, since the ratios of pyruvic acid to lactic acid and of lactamide to lactic acid distilled is higher in the first overhead fractions and decreases as the run progresses. Thus the lactamide—diethylbenzene azeotrope is preferentially removed in the early fractions. This demonstrates that lactamide can be purified from lactic acid via a fractional azeotropic distillation process.

EXAMPLE 2
Recovery of Lactic Acid from a Feed Stream Comprising Lactic Acid Using dodecane as an Azeotroping Agent in a One Day Batch Process without Reflux A 250 ml three neck flask with a stirrer was charged with reagents. The initial batch charge was 50.0 grams of 98% 1-dodecane and 40.0 grams of 88% lactic acid in water. The system was heated under vacuum, and the system pressure was −25.4 inches Hg gauge. The overhead vapor was drawn to a condenser and condensate receiver. There was little or

| OVERHEAD PRODUCT CONDENSATE HEAVY PHASE COMPONENT CONCENTRATIONS (% w/w) | | | | | | |
|---|---|---|---|---|---|---|
| | Feed (Heavy Phase) | OV1 (Heavy Phase) | OV2 (Heavy Phase) | OV3 (Heavy Phase) | OV4 (Heavy Phase) | OV5 (Heavy Phase) |
| Lactic acid | 60.3 | 0.2 | 14.9 | 39.7 | 50.7 | 54.2 |
| Pyruvic acid | 0.109 | 0.00776 | 0.280 | 0.365 | 0.375 | 0.228 |
| Diethyl-benzene | 0 | 0 | 0 | 0 | 0 | 0 |
| Water | 40 | 100 | 85 | 60 | 49 | 45 |

In this example water distills in the overhead first and more lactic acid distills as the run progresses. Also, the ratio of pyruvic acid to lactic acid distilled is higher in the first overhead fractions and decreases as the run progresses. Lactic acid is readily distilled to the overhead heavy phase, and the later overhead heavy phases are rich in lactic acid.

EXAMPLE 3
Recovery of Lactic Acid from a Feed Stream Comprising Lactic Acid Using diethylbenzene as an Azeotroping Agent in a One Day Continuous Process without Reflux A 250 ml three neck flask with a stirrer was charged with reagents. The system pressure was −25.7 inches Hg gauge. The overhead vapor was drawn to a condenser and condensate receiver. There was little or no reflux. The typical liquid temperature during the run was 105° C. The vapor immediately above the liquid was 102° C. The vapor at the top of the head prior to entering the condenser was 99° C.

There was an initial batch charge of 43.7 grams pure diethylbenzene. The system was heated under vacuum until condensate flow just started and then the continuous feeds were started.

The continuous feeds were made at the following average rates: pure diethylbenzene 84 grams per 6 hours and 50% lactic acid in water 14 grams per 6 hours.

One overhead condensate sample ("OV") was collected. The sample consisted of a light phase (e.g. comprising azeotroping agent) and a heavy phase (e.g. comprising lactic acid). The phases were separated and samples from each phase were analyzed by HPLC. The first diethylbenzene condensate ("Initial DEB Out") was collected before continuous feeds were started. The undistilled residue left in the flask, "BTMS", was also analyzed.

OVERALL MASS BALANCE

|  | Feed | OV | BTMS | Initial DEB OUT |
|---|---|---|---|---|
| Mass of light phase (grams) | 127.5 | 85.9 | 0 | 41.1 |
| Mass of heavy phase (grams) | 14.0 | 9.0 | 3.9 | 0 |

OVERHEAD PRODUCT CONDENSATE HEAVY PHASE COMPONENT CONCENTRATIONS (% w/w)

|  | Feed (Heavy Phase) | OV (Heavy Phase) |
|---|---|---|
| Lactic acid | 52.4 | 36.5 |
| Diethylbenzene | 0 | 0.5 |
| Water | 43.0 | 60.9 |

In this example the lactic acid is easily distilled into the overhead phase and the overhead heavy phase is rich in lactic acid, typically around 37% w/w lactic acid.

The yield of lactic acid recovered from the overhead heavy phases was 45.1 wt % of the lactic acid present in the feed.

EXAMPLE 4
Recovery of Lactic Acid from a Feed Stream Comprising Lactic Acid and Five Impurities Using diethylbenzene as an Azeotroping Agent in a Three Day Continuous Process without Reflux A 250 ml three neck flask with a stirrer was charged with reagents plus the undistilled residue from the previous day. At the end of each day's run, the undistilled residue was used as a charge for the next day's run. The system pressure was −25.7 inches Hg gauge. The overhead vapor was drawn to a condenser and condensate receiver. There was little or no reflux. The typical liquid temperature during the run was 100° C. The vapor immediately above the liquid was 87° C. The vapor at the top of the head prior to entering the condenser was 77° C.

At the beginning of each day, the pot was charged with diethylbenzene and the undistilled residue from the previous day. There was an initial batch charge of 8.6 grams pure diethylbenzene on day 1, 8.4 grams pure diethylbenzene on day 2, and 8.8 grams pure diethylbenzene on day 3. The system was heated under vacuum until condensate flow just started and then the continuous feeds were started, on each day.

The continuous feeds were made at the following average rates: pure diethylbenzene 290 grams per 21 hours and 50% lactic acid in water plus 5 impurities 59 grams per 21 hours.

The following table shows the concentration of the impurities in the 50% lactic acid in the feed.

| Impurity | Concentration (g/L) |
|---|---|
| Malic acid | 1.250 |
| Succinic acid | 1.250 |
| Maltose | 10.000 |
| Glycerol | 5.240 |
| 2,3-Butanediol | 0.800 |

Four overhead condensate samples ("OV1" to "OV4") were collected. The samples consisted of a light phase (e.g. comprising azeotroping agent) and a heavy phase (e.g. comprising lactic acid). The phases were separated and samples from each phase were analyzed by HPLC. The undistilled residue left in the flask, "BTMS", was also analyzed.

OVERALL MASS BALANCE

|  | Feed | OV1 | OV2 | OV3 | OV4 | BTMS |
|---|---|---|---|---|---|---|
| Mass of light phase (grams) | 316.1 | 86.3 | 81.6 | 29.1 | 106.7 | 0 |
| Mass of heavy phase (grams) | 59.4 | 10.1 | 11.0 | 3.8 | 13.0 | 11.8 |

OVERHEAD PRODUCT CONDENSATE HEAVY PHASE COMPONENT CONCENTRATIONS (% w/w)

|  | Feed (Heavy Phase) | OV1 (Heavy Phase) | OV2 (Heavy Phase) | OV3 (Heavy Phase) | OV4 (Heavy Phase) | BTMS (Heavy Phase) |
|---|---|---|---|---|---|---|
| Lactic acid | 46.6 | 34.2 | 34.3 | 40.5 | 34.8 | 33.2 |
| Diethylbenzene | 0 | 0.5 | 0.5 | 0.5 | 0.5 | 0 |
| Water | 48.8 | 61.3 | 55.9 | 52.1 | 59.9 | 24.0 |
| Malic acid | 0.15 | 0 | 0.02 | ap | 0.01 | ap |

In this example the lactic acid is easily distilled into the overhead phase and the overhead heavy phase is rich in lactic acid, on average the overhead heavy phase contained around 34% w/w lactic acid.

The yield of lactic acid was 42.2% on the first day, 57.0% on the second day, and 49.2% on the third day.

FURTHER PURITY ANALYSIS

| Sample | Glucose ppm | Glycerol ppm | Maltose ppm | Maltotriose ppm | Maltotetraose ppm | Malate ppm | Pyruvate ppm | Succinate ppm | Acetic ppm | Formic ppm | Lactic ppm |
|---|---|---|---|---|---|---|---|---|---|---|---|
| OV1 (Heavy Phase) | 1.3 | 2 | <1.0 | none detected | none detected | <5 | 10.6 | <5 | 1.8 | 3 | 3250 |
| Feed (Heavy Phase) | <1.0 | 51 | 98 | none detected | none detected | 10.4 | 3.8 | 13.6 | <1.0 | 2.3 | 4810 |
| OV2 (Heavy Phase) | <1.0 | 6.8 | 5.5 | none detected | none detected | <5 | 10.6 | <5 | 1.6 | 3.2 | 3910 |
| OV3 (Heavy Phase) | <1.0 | 5.7 | 7 | none detected | none detected | <5 | 11 | <5 | 1.6 | 2.9 | 3625 |
| Bottoms Sample | 24 | 230 | 260 | 54 | 45 | 51.8 | 13.2 | 56.4 | <5 | <10 | 16635 |

EXAMPLE 5

Recovery of Lactic Acid from a Feed Stream Comprising Lactic Acid and Six Impurities Using diethylbenzene as an Azeotroping Agent in a Two Day Continuous Process without Reflux A 250 ml three neck flask with a stirrer was charged with reagents plus the undistilled residue from the previous day. The system pressure was −25.7 inches Hg gauge. The overhead vapor was drawn to a condenser and condensate receiver. There was little or no reflux. The typical liquid temperature during the run was 125° C. The vapor immediately above the liquid was 114° C. The vapor at the top of the head prior to entering the condenser was 84° C.

At the beginning of day 2, the pot was charged with diethylbenzene and the undistilled residue from the previous day (similar to Example 2 above). The undistilled residue from first day was used to charge the pot for the second day. There was an initial batch charge of 8.8 grams pure diethylbenzene on day 1, but there was no diethylbenzene charge on day 2. The system was heated under vacuum until condensate flow just started and then the continuous feeds were started, on each day.

The continuous feeds were made at the following average rates: pure diethylbenzene 228 grams per 15 hours and 50% lactic acid in water plus 6 impurities 34 grams per 15 hours.

The following table shows the concentration of the impurities in the 50% lactic acid in water feed.

| Impurity | Concentration (g/L) |
|---|---|
| Malic acid | 1.250 |
| Succinic acid | 1.250 |
| Maltose | 10.000 |
| Glycerol | 5.240 |
| 2,3-Butanediol | 0.800 |
| Glucose | 2.000 |

Two overhead condensate samples ("OV1" and "OV2") were collected. The samples consisted of a light phase (e.g. comprising azeotroping agent) and a heavy phase. The phases were separated and samples from each phase were analyzed by HPLC. The undistilled residue left in the flask, "BTMS", was also analyzed.

OVERALL MASS BALANCE

| | Feed (Both Phases) | BTMS IN (Heavy Phase) | OV1 (Both Phases) | OV2 (Both Phases) | BTMS OUT (Both Phases) |
|---|---|---|---|---|---|
| Mass of light phase (grams) | 236.3 | 0 | 132.5 | 84.6 | 12.3 |
| Mass of heavy phase (grams) | 34.1 | 11.3 | 15.8 | 7.6 | 15.3 |

OVERHEAD PRODUCT CONDENSATE HEAVY PHASE COMPONENT CONCENTRATIONS (% w/w)

| | Feed (Heavy Phase) | BTMS IN (Heavy Phase) | OV1 (Heavy Phase) | OV2 (Heavy Phase) | BTMS (Heavy Phase) |
|---|---|---|---|---|---|
| Lactic acid | 42.5 | 33.2 | 41.2 | 30.8 | 27.0 |
| Diethylbenzene | 0 | 0 | 0.5 | 0.5 | 0 |
| Water | 47.8 | 24.0 | 50.8 | 61.9 | 42.9 |

In this example the lactic acid is easily distilled into the overhead phase and the overhead heavy phase is rich in lactic acid, typically around 36% w/w lactic acid.

The yield of lactic acid relative to what had been present in the feed was 85.5% on the first day and 34.2% on the second day.

About 1 milligram of tiny white, flaky solids per 1 gram of lactic acid were formed at the interface of the two overhead phases, in both samples. The solids dissolved readily in methanol.

EXAMPLE 6

Recovery of Lactic Acid from a Feed Stream Comprising Lactic Acid and Six Impurities Using Recycled diethylbenzene as an Azeotroping Agent in a One Day Continuous Process without Reflux A 250 ml three neck flask with a stirrer was charged with reagents. The system pressure was −22.5 inches Hg gauge. The overhead vapor was drawn to a condenser and condensate receiver. There was little or no reflux. The typical liquid temperature during the run was 130° C. The vapor immediately above the liquid was 130° C. The vapor at the top of the head prior to entering the condenser was 109° C.

Initially, the pot was charged with 42.9 grams of recycled diethylbenzene. The diethylbenzene had been recycled from the light overhead phases of previous experiments. The system was heated under vacuum until condensate flow just started and then the continuous feeds were started.

The continuous feed flow rates were doubled with respect to the rates in previous examples. The continuous feeds were made at the following average rates: recycled diethylbenzene 339 grams per 7 hours and 50% lactic acid in water plus 6 impurities 64 grams per 7 hours.

The following table shows the concentration of the impurities in the 50% lactic acid in the feed.

| Impurity | Concentration (g/L) |
| --- | --- |
| Malic acid | 1.250 |
| Succinic acid | 1.250 |
| Maltose | 10.000 |
| Glycerol | 5.240 |
| 2,3-Butanediol | 0.800 |
| Glucose | 2.000 |

Two overhead condensate samples ("OV1" and "OV2") were collected. The samples consisted of a light phase (e.g. comprising azeotroping agent) and a heavy phase. The phases were separated and samples from each phase were analyzed by HPLC. The undistilled residue left in the flask, "BTMS", was also analyzed.

OVERALL MASS BALANCE

|  | Feed | OV1 | OV2 | BTMS |
| --- | --- | --- | --- | --- |
| Mass of light phase (grams) | 382.1 | 195.8 | 107.5 | 70.9 |
| Mass of heavy phase (grams) | 64.2 | 26.6 | 20.0 | 18.2 |

OVERHEAD PRODUCT CONDENSATE HEAVY PHASE COMPONENT CONCENTRATIONS (% w/w)

|  | Feed (Heavy Phase) | OV1 (Heavy Phase) | OV2 (Heavy Phase) | BTMS (Heavy Phase) |
| --- | --- | --- | --- | --- |
| Lactic acid | 45.9 | 31.0 | 21.8 | 49.5 |
| Diethylbenzene | 0 | 0.5 | 0.5 | 0 |
| Water | 47.4 | 66.8 | 76.7 | 2.0 |

In this example, the lactic acid is easily distilled into the overhead phase and the overhead heavy phase is rich in lactic acid, on average around 26% w/w lactic acid.

The yield of lactic acid relative to the lactic acid present in the feed was 42.8%.

About 1 milligram of tiny white, flaky solids per 1 gram of lactic acid were formed at the interface of the two overhead phases. The solids dissolved readily in isopropanol and acetonitrile.

EXAMPLE 7
Recovery of Lactic Acid from a Feed Stream Comprising Lactic Acid and One Impurity Using diethylbenzene as an Azeotroping Agent in a One Day Continuous Process without Reflux This example used only one impurity, glucose, to discover if the solids formed in the previous two examples would form again.

A 250 ml three neck flask with a stirrer was charged with reagents. The system pressure was −22.6 inches Hg gauge. The overhead vapor was drawn to a condenser and condensate receiver. There was little or no reflux. The typical liquid temperature during the run was 115° C. The vapor immediately above the liquid was 109° C. The vapor at the top of the head prior to entering the condenser was 107° C.

Initially, the pot was charged with 43.3 grams of recycled diethylbenzene. The system was heated under vacuum until condensate flow just started and then the continuous feeds were started.

The continuous feeds were made at the following average rates: recycled diethylbenzene 342 grams per 8 hours and 50% lactic acid in water plus glucose 49 grams per 8 hours.

The following table shows the concentration of the impurities in the 50% lactic acid in water feed.

| Impurity | Concentration (g/L) |
| --- | --- |
| Glucose | 2.000 |

Two overhead condensate samples ("OV1" and "OV2") were collected. The samples consisted of a light phase (e.g. comprising azeotroping agent) and a heavy phase.

The phases were separated and samples from each phase were analyzed by HPLC. The undistilled residue left in the flask, "BTMS", was also analyzed.

OVERALL MASS BALANCE

|  | Feed | OV1 | OV2 | BTMS |
| --- | --- | --- | --- | --- |
| Mass of light phase (grams) | 385.3 | 201.9 | 106.6 | 73.8 |
| Mass of heavy phase (grams) | 49.0 | 20.2 | 12.2 | 13.0 |

OVERHEAD PRODUCT CONDENSATE HEAVY PHASE COMPONENT CONCENTRATIONS (% w/w)

|  | Feed (Heavy Phase) | OV1 (Heavy Phase) | OV2 (Heavy Phase) | BTMS (Heavy Phase) |
| --- | --- | --- | --- | --- |
| Lactic acid | 48.3 | 31.0 | 34.7 | 47.7 |
| Diethylbenzene | 0 | 0.5 | 0.5 | 0 |
| Water | 44.2 | 67.0 | 63.6 | 2.9 |

In this example, the lactic acid is easily distilled into the overhead phase and the overhead heavy phase is rich in lactic acid, on average around 33% w/w lactic acid.

The yield of lactic acid relative to the lactic acid present in the feed was 44.4%.

About 1 milligram of white, flaky solids per 1 gram of lactic acid were formed at the interface of the two overhead phases. The solids were small and difficult to collect.

EXAMPLE 8

Recovery of Lactic Acid from a Feed Stream Comprising Lactic Acid and No Impurities Using diethylbenzene as an Azeotroping Agent in a One Day Continuous Process without Reflux In order to determine if the solids formed in the previous examples were lactic acid derivatives, this example used no impurities in the 50% lactic acid in water feed.

A 250 ml three neck flask with a stirrer was charged with reagents. The system pressure was −22.8 inches Hg gauge. The overhead vapor was drawn to a condenser and condensate receiver. There was little or no reflux. The typical liquid temperature during the run was 115° C. The vapor immediately above the liquid was 109° C. The vapor at the top of the head prior to entering the condenser was 107° C.

Initially, the pot was charged with 43.1 grams of recycled diethylbenzene. The system was heated under vacuum until condensate flow just started and then the continuous feeds were started.

The continuous feeds were made at the following average rates: recycled diethylbenzene 396 grams per 8 hours and 50% lactic acid in water 57 grams per 8 hours.

Two overhead condensate samples ("OV1" and "OV2") were collected. The samples consisted of a light phase (e.g. comprising azeotroping agent) and a heavy phase. The phases were separated and samples from each phase were analyzed by HPLC. The undistilled residue left in the flask, "BTMS", was also analyzed.

OVERALL MASS BALANCE

| | Feed | OV1 | OV2 | BTMS |
|---|---|---|---|---|
| Mass of light phase (grams) | 439.3 | 280.6 | 95.2 | 68.8 |
| Mass of heavy phase (grams) | 57.0 | 24.3 | 8.1 | 17.4 |

OVERHEAD PRODUCT CONDENSATE HEAVY PHASE COMPONENT CONCENTRATIONS (% w/w)

| | Feed (Heavy Phase) | OV1 (Heavy Phase) | OV2 (Heavy Phase) | BTMS (Heavy Phase) |
|---|---|---|---|---|
| Lactic acid | 47.9 | 36.4 | 35.9 | 46.1 |
| Diethylbenzene | 0 | 0.5 | 0.5 | 0 |
| Water | 44.8 | 31.4 | 61.9 | 4.0 |

In this example, the lactic acid is easily distilled into the overhead phase and the overhead heavy phase is rich in lactic acid, typically around 36% w/w lactic acid.

The yield of lactic acid relative to lactic acid present in the feed was 43.1%.

About 1 milligram of white, flaky solids per 1 gram of lactic acid were formed at the interface of the two overhead phases. The solids were small and difficult to collect by gravity and vacuum filtration.

EXAMPLE 9

Recovery of Lactic Acid from a Feed Stream Comprising Lactic Acid and No Impurities Using diethylbenzene as an Azeotroping Agent in a One Day Continuous Process without Reflux In order to generate more of the solids, this example used continuous feed flow rates that were twice the flow rates in the previous example.

A 250 ml three neck flask with a stirrer was charged with reagents. The system pressure was −22.8 inches Hg gauge. The overhead vapor was drawn to a condenser and condensate receiver. There was little or no reflux. The typical liquid temperature during the run was 115° C. The vapor immediately above the liquid was 114° C. The vapor at the top of the head prior to entering the condenser was 113° C.

Initially, the pot was charged with 42.9 grams of fresh diethylbenzene. The system was heated under vacuum until condensate flow just started and then the continuous feeds were started.

The continuous feeds were made at the following average rates: diethylbenzene 637 grams per 8 hours and 50% lactic acid in water 108 grams per 8 hours. In this case, the diethylbenzene used was a mixture of fresh and recycled diethylbenzene. The recycled diethylbenzene was obtained as the light overhead phase from an earlier experiment.

One overhead condensate sample ("OV") was collected. The sample consisted of a light phase (e.g. comprising azeotroping agent) and a heavy phase. The phases were separated and samples from each phase were analyzed by HPLC. The undistilled residue left in the flask, "BTMS", was also analyzed.

OVERALL MASS BALANCE

| | Feed | OV | BTMS |
|---|---|---|---|
| Mass of light phase (grams) | 679.4 | 575.1 | 102.2 |
| Mass of heavy phase (grams) | 107.4 | 73.5 | 32.7 |

OVERHEAD PRODUCT CONDENSATE HEAVY PHASE COMPONENT CONCENTRATIONS (% w/w)

| | Feed (Heavy Phase) | OV (Heavy Phase) | BTMS (Heavy Phase) |
|---|---|---|---|
| Lactic acid | 47.9 | 27.6 | 47.5 |
| Diethylbenzene | 0 | 0.5 | 0 |
| Water | 44.8 | 70.5 | 5.1 |

In this example, the lactic acid is easily distilled into the overhead phase and the overhead heavy phase is rich in lactic acid, typically around 28% w/w lactic acid.

The yield of lactic acid relative to the lactic acid present in the feed was 39.5%.

About 1 milligram of white, flaky solids per 2 grams of lactic acid were formed at the interface of the two overhead phases. The solids were small and difficult to collect by gravity and vacuum filtration. The amount of solids produced did not increase proportionally with the increased continuous flow rates.

EXAMPLE 10

Recovery of Lactic Acid from a Feed Stream Comprising Lactic Acid and Five Impurities Using diethylbenzene as an Azeotroping Agent in a One Day Continuous Process without Reflux The purpose of this example was to produce the solids formed by the previous examples with the 50% lactic acid feed with 5 impurities.

A 250 ml three neck flask with a stirrer was charged with reagents. The system pressure was −22.1 inches Hg gauge. The overhead vapor was drawn to a condenser and condensate receiver. There was little or no reflux. The typical liquid temperature during the run was 125° C. The vapor immediately above the liquid was 123° C. The vapor at the top of the head prior to entering the condenser was 109° C.

Initially, the pot was charged with 43.0 grams of recycled diethylbenzene. The system was heated under vacuum until condensate flow just started and then the continuous feeds were started.

The continuous feeds were made at the following average rates: recycled diethylbenzene 414 grams per 7 hours and 50% lactic acid in water plus 5 impurities 52 grams per 7 hours.

The following table shows the concentration of the impurities in the 50% lactic acid in water feed.

| Impurity | Concentration (g/L) |
| --- | --- |
| Malic acid | 1.250 |
| Succinic acid | 1.250 |
| Maltose | 10.000 |
| Glycerol | 5.240 |
| 2,3-Butanediol | 0.800 |

One overhead condensate sample ("OV") was collected. The sample consisted of a light phase (e.g. comprising azeotroping agent) and a heavy phase. The phases were separated and samples from each phase were analyzed by HPLC. The undistilled residue left in the flask, "BTMS", was also analyzed.

| OVERALL MASS BALANCE | | | |
| --- | --- | --- | --- |
| | Feed | OV | BTMS |
| Mass of light phase (grams) | 456.7 | 359.5 | 92.5 |
| Mass of heavy phase (grams) | 52.3 | 43.5 | 10.7 |

| OVERHEAD PRODUCT CONDENSATE HEAVY PHASE COMPONENT CONCENTRATIONS (% w/w) | | | |
| --- | --- | --- | --- |
| | Feed (Heavy Phase) | OV (Heavy Phase) | BTMS (Heavy Phase) |
| Lactic acid | 44.7 | 33.5 | 36.8 |
| Diethylbenzene | 0 | 0.5 | 0 |
| Water | 48.5 | 64.4 | 2.8 |

In this example, the lactic acid is easily distilled into the overhead phase and the overhead heavy phase is rich in lactic acid, on average around 34% w/w lactic acid.

The yield of lactic acid in the overhead heavy phases relative to the lactic acid present in the feed was 62.2%.

About 1 milligram of tiny white, flaky solids per 1 gram of lactic acid were formed at the interface of the two overhead phases. The solids were difficult to recover and, therefore, were not analyzed.

EXAMPLE 11

Recovery of Lactic Acid from a Feed Stream Comprising Bottoms from Example 7 Using diethylbenzene as an Azeotroping Agent in a One Day Continuous Process without Reflux The purpose of this example was to achieve 100% lactic acid yield by using water to chase the remaining lactic acid out of the pot.

A 250 ml three neck flask with a stirrer was charged with the bottoms light phase (e.g. comprising azeotroping agent) and heavy phases from Example 7. The system pressure initially was −20.5 inches Hg gauge, but after two hours the vacuum pump failed. A new vacuum pump was installed, delivering a vacuum of −22.9 inches Hg gauge. The overhead vapor was drawn to a condenser and condensate receiver. There was little or no reflux. The typical liquid temperature during the run was 125° C. The vapor immediately above the liquid was 123° C. The vapor at the top of the head prior to entering the condenser was 109° C.

Initially, the pot was charged with 77.1 grams of bottoms light phase (e.g. comprising azeotroping agent) and 27.6 grams of bottoms heavy from Example 7. These bottom phases were produced from a distillation of no impurities in the 50% lactic acid in water feed. The system was heated under vacuum until condensate flow just started and then the continuous feeds were started.

The continuous feeds were made at the following average rates: fresh diethylbenzene 918 grams per 9 hours and water 73 grams per 9 hours.

Six overhead condensate samples ("OV1" to "OV6") were collected. A large amount of pot liquid flashed overhead ("Flash") when the new pump was installed on Jun. 28, 2000. The heavy phase (e.g. comprising lactic acid) that flashed overhead was returned to the pot for distillation on Jun. 29, 2000. The light phase (e.g. comprising azeotroping agent) was not returned to the pot or analyzed. The overhead samples consisted of a light phase (e.g. comprising azeotroping agent) and a heavy phase. The phases were separated and samples from each phase were analyzed by HPLC. The undistilled residue left in the flask, "BTMS", was also analyzed.

| OVERALL MASS BALANCE | | | | | | | | | |
|---|---|---|---|---|---|---|---|---|---|
|  | Feed | OV1 | Flash | OV2 | OV3 | OV4 | OV5 | OV6 | BTMS |
| Mass of phase (grams) | 995.0 | 82.3 | 60.9 | 118.9 | 156.2 | 183.9 | 169.1 | 164.8 | 47.9 |
| Mass of heavy phase (grams) | 100.4 | 15.3 | 0 | 22.7 | 12.3 | 11.6 | 10.1 | 15.7 | 12.1 |

| OVERHEAD PRODUCT CONDENSATE HEAVY PHASE COMPONENT CONCENTRATIONS (% w/w) | | | | | | | | |
|---|---|---|---|---|---|---|---|---|
|  | Feed | OV1 | OV2 | OV3 | OV4 | OV5 | OV6 | BTMS |
| Lactic acid | 47.5 | 27.4 | 5.8 | 20.0 | 17.1 | 5.1 | 1.7 | 36.8 |
| Diethylbenzene | 0 | 0 | 0 | 0 | 0 | 0 | 0 | 0 |
| Water | 5.1 | 70.2 | 88 | 75.7 | 73.3 | 90.0 | 91.5 | 2.8 |

Saponification revealed significant lactic dimer, trimer, and tetramer left in the bottoms heavy phase (e.g. comprising lactic acid) after this water chase. Saponification was used to measure all lactic species as monomer in the bottoms. Saponification of the bottoms heavy product showed that any suitable hydrolysis method could release all the lactic values as monomer.

Significant lactic acid was present in the early overheads, compared to the later overheads. More water appeared to have distilled overhead in the later samples. "OV2" was the first sample taken after the flashing occurred and the installation of the new pump. The yield of lactic acid relative to the amount of lactic acid present in the feed was 84.5%.

About 0.5 milligrams of tiny white, flaky solids were formed at the interface of the two overhead phases. The solids were difficult to recover and, therefore, were not analyzed.

EXAMPLE 12
Recovery of Lactic Acid from a Feed Stream Comprising Lactic Acid and No Impurities Using diethylbenzene as an Azeotroping Agent in Three One-day Batch Processes with Reflux The same experiment was run for three days, but only the data from one day was useful.

A 250 ml three neck flask with a stirrer was charged with reagents. The system pressure was −22.8 inches Hg gauge. The overhead vapor was drawn to a condenser and condensate receiver. There was reflux through a short packed column. The column was glass, packed with 0.16 inch×0.16 inch stainless steel saddles that had crimped indentations on them. The height of the packed section was bout 2 inches, representing 1 to 4 theoretical stages under these conditions. The typical liquid temperature during the run was 128° C. The vapor immediately above the liquid was 128° C. The vapor at the top of the head, above the packed column, prior to entering the condenser was approximately 60° C.

There was an initial batch charge of 86.3 grams of pure diethylbenzene and 11.1 grams of 50% lactic acid in water. The system was heated under vacuum.

Six overhead condensate samples ("OV1" to "OV6") were collected. The samples consisted of a light phase (e.g. comprising azeotroping agent) and a heavy phase. The phases were separated and samples from each phase were analyzed by HPLC. The undistilled residue left in the flask, "BTMS", was also analyzed.

| OVERALL MASS BALANCE | | | | | | | | |
|---|---|---|---|---|---|---|---|---|
|  | Feed | OV1 | OV2 | OV3 | OV4 | OV5 | OV6 | BTMS |
| Mass of light phase (grams) | 86.3 | 0.9 | 2.0 | 8.2 | 9.2 | 9.0 | 1.2 | 55.2 |
| Mass of heavy phase (grams) | 11.1 | 2.8 | 2.3 | 0.6 | 0.9 | 0.4 | 0.3 | 3.6 |

| OVERHEAD PRODUCT CONDENSATE HEAVY PHASE COMPONENT CONCENTRATIONS (% w/w) | | | | | | | | |
|---|---|---|---|---|---|---|---|---|
|  | Feed | OV1 | OV2 | OV3 | OV4 | OV5 | OV6 | BTMS |
| Lactic acid | 50.1 | 7.5 | 1.4 | 13.8 | 54.2 | 59.0 | 59.2 | 16.2 |
| Diethylbenzene | 0 | 0 | 0 | 0 | 0 | 0 | 0 | 0 |
| Water | 46.6 | 90.0 | 98.3 | 85.5 | 44.7 | 39.9 | 39.4 | 1.2 |

In this example, water is the first component to distill overhead, with little lactic acid, while more lactic acid and less water distills as the run progresses. The lactic acid goes from a minimum of approximately 1.5% w/w to a maximum of 60% w/w of the overhead heavy phase.

The yield of lactic acid in the overhead heavy phase relative to the amount present in the feed was 21.6%.

EXAMPLE 13
Recovery of Lactic Acid from a Feed Stream Comprising Lactic Acid (About 50 wt %), Water, and 10 Impurities Using 1-dodecane as an Azeotroping Agent in Continuous Batch Process with Reflux A three-neck flask was charged with 10 grams of 50% lactic acid in water containing 10 impurities and 90 grams of dodecane. Two columns were placed on top of the three-neck flask. Both columns were packed with two inches of stainless steel metal-dump packing. A condenser leading into a collection flask was attached to the top column. The columns and three-neck flask were insulated. Four temperatures were monitored: pot liquid, pot vapor, an intermediate vapor at the middle point between the two columns, and an overhead vapor at the top of the apparatus. The intermediate and overhead temperatures were recorded to determine if there was an azeotrope. 50% lactic acid feed in water with 10 impurities and 1-dodecane were used as the continuous feeds. The system pressure was −24.2 inches Hg. The approximate temperatures attained were: 150° C. for the pot liquid, 150° C. for pot vapor, 137° C. for the intermediate vapor, and 112° C. for the overhead vapor.

The first heavy overhead in the table below is a fraction collected early in the azeotropic distillation, while the second heavy overhead is a fraction collected later in the same azeotropic distillation. Some of the samples were analyzed under less dilution in order to magnify impurities. Pyruvic acid increased in concentration for both overhead samples, compared to the feed. HPLC analysis indicated that the malic acid impurity did not distill overhead, but remained in the bottoms heavy phase. HPLC analysis of the overhead heavy samples and the bottoms heavy sample showed numerous unknown peaks, possibly due to impurities.

The bottoms heavy product indicated low concentrations of lactic monomer and dimer. Before saponification of the bottoms heavy product, the lactic species closure was 48%. After saponification, the lactic species closure was 114%. Most of the lactic acid in the bottoms heavy product was in the form of oligomers. Saponification of the second overhead heavy phase did not indicate more lactic acid than before saponification. The lactic acid equivalent yield for the overhead heavy phases was 17%. The feed was 49.9% lactic acid equivalent by weight. The first overhead heavy was 15.75% lactic acid equivalent (e.g. comprises lactic acid species of free lactic acid, dimers, trimers and oligomers of lactic acid) by weight. The second overhead heavy was 45.62% lactic acid equivalent by weight.

PURITY DATA

|  |  | 50 wt % Lactic acid feed + impurities | 1st overhead heavy from distillation | 2nd overhead heavy from distillation | bottoms heavy |
|---|---|---|---|---|---|
| Glucose | μg/ml | 9370 | <50 | <50 | 630 |
| Glycerol | μg/ml | 28610 | 58 | 143 | 23890 |
| Maltose | μg/ml | 860 | <50 | <50 | 470 |
| Mannitol | μg/ml | 21230 | <50 | <50 | 15800 |
| Formate | μg/ml | 130 | 200 | 240 | 100 |
| Malate | μg/ml | 1065 | <100 | <100 | 890 |
| Pyruvate | μg/ml | 170 | 210 | 390 | 540 |
| Succinate | μg/ml | 1650 | <100 | <100 | 1510 |
| Acetic | μg/ml | 252 | 395 | 470 | 500 |
| Lactic | wt % | 48.18 | 15.31 | 45.75 | 91.84 |

In the overheads glucose, glycerol, maltose, mannitol, malic acid, and succinic acid were all effectively removed. Concentrations of formic acid, pyruvic acid, and acetic acid all increased modestly over the concentrations in the feed. The rejection of glycerol in the $1^{st}$ overhead is 99.8 wt % of the glycerol that was initially present in the feed stream, and 99.5 wt % in the $2^{nd}$ overhead.

EXAMPLE 14
Recovery of Lactic Acid from a Feed Stream Comprising Lactic Acid (About 70 wt %), Water, and 10 Impurities Using 1-dodecane as an Azeotroping Agent in Continuous Batch Process with Reflux The apparatus used was the same as in Example 13. The pot was charged with 10 grams of 70% lactic acid in water with 10 impurities and 90 grams of dodecane. 70% lactic acid feed in water with 10 impurities and dodecane were used as the continuous feeds. The system pressure was −24.7 inches Hg. The approximate temperatures attained were: 147° C. for the pot liquid, 140° C. for pot vapor, 132° C. for the intermediate vapor, and 60° C. for the overhead vapor.

Pyruvic acid increased in concentration for both overhead samples, compared to the feed. HPLC analysis indicated that the malic acid impurity did not distill overhead, but remained in the bottoms heavy phase. HPLC analysis of the overhead heavy samples and the bottoms heavy sample showed numerous unknown peaks, possibly due to impurities.

The bottoms heavy product indicated low concentrations of lactic monomer and dimer. Before saponification of the bottoms heavy product, the lactic species closure was 54%. The lactic acid equivalent yield for the overhead heavy phases was 30%. The feed was 67.5% lactic acid equivalent by weight. The first overhead heavy was 50.5% lactic acid equivalent by weight. The second overhead heavy was 61.0% lactic acid equivalent by weight.

PURITY DATA

|  |  | 70 wt % Lactic acid feed + impurities | 1st Overhead heavy from distillation | 2nd overhead heavy from distillation | bottoms heavy |
|---|---|---|---|---|---|
| Glucose | μg/ml | 12210 | <50 | <50 | 630 |
| Glycerol | μg/ml | 36660 | 1100 | 4600 | 13330 |
| Maltose | μg/ml | 1140 | <50 | <50 | 335 |
| Mannitol | μg/ml | 27550 | <50 | <50 | 11730 |
| Formate | μg/ml | 130 | 200 | 300 | 185 |
| Malate | μg/ml | 1680 | <100 | <100 | 1450 |
| Pyruvate | μg/ml | 205 | 580 | 350 | 510 |
| Succinate | μg/ml | 2320 | <100 | 140 | 2425 |
| Acetic | μg/ml | 355 | 540 | 510 | 290 |
| Lactic | wt % | 73.94 | 51.87 | 56.63 | 89.93 |

Glucose, maltose, mannitol, malic acid, and succinic acid were all largely removed in the overhead while 88% of the glycerol in the feed was removed. The concentrations of formic acid, pyruvic acid, and acetic acid all increased to approximately double the concentration in the feed. The rejection of glycerol in the first overhead is about 97 wt % of the glycerol that was initially present in the feed stream, and about 87.5 wt % in the $2^{nd}$ overhead. Comparing these results to those of Example 13, there is improved glycerol rejection in the azeotropic distillation, when the feed stream comprises higher wt % water.

EXAMPLE 15
Simulation of Lactic Acid Distillation with Low Reflux and without an Azeotroping Agent An ASPEN simulation was conducted analyzing a simple commercial distillation system having four theoretical equilibrium stages (2, 3, 4 and 5) and a condenser, which was configured to act as vapor liquid equilibrium stage (1). This could be a tray tower with 10 trays each with a contacting efficiency of 50%. A crude lactic acid solution was introduced at 15,000 lb/hr to the middle theoretical stage (3). This solution contained 9000 lb/hr of monomeric lactic acid, 2844 lb/hr water and other components. The lactic acid solution was preheated to 110° C. A stream of 267 lbmol/hour of nitrogen stripping gas at 158° C. was introduced to the bottom stage (5). This stage was also heated with 1.84 MM BTU/hr. The middle stage (3) was a small pumparound heater supplying an additional 0.57 MM BTU/hr to that stage. The top stage or condenser (1) had a small cooling load of −0.099 MM BTU/hr to provide a very small reflux to the system. The system was operated at a moderate vacuum of 200 mmHg. Component vapor pressures used were based on literature data and correlations of available data.

It was predicted that 1561 lb/hr of lactic acid could be removed into the overhead product vapor stream as long as holdup times in the system were very short such that there was insufficient time for conversion of the lactic acid monomer to heavy dimer. Overhead temperature was 77.0° C. The ratio of water to nitrogen was such that the system was kept relatively cool, and this kept rates of oligomerization low.

While in practice, it can be difficult to achieve these overhead distillation rates using nitrogen stripping gas due to oligomerization, this example is useful for comparison with Example 16, which embodies the same assumptions but with high reflux.

EXAMPLE 16
Simulation of Lactic Acid Distillation with High Reflux and without an Azeotroping Agent An ASPEN simulation was performed using the same conditions and apparatus as were used in Example 15, but a different reflux was used. The condenser duty was −0.599 MM BTU/hr. The overhead lactic acid rate dropped to 729 lb/hr. In this case, as reflux was applied, the less volatile species, lactic acid, was knocked back and condensed. Overhead temperature was 78.2° C. Comparison of this example with example 15 shows that the introduction of reflux in the case of non-azeotropic system leads to rejection of the lactic acid from the vapor phase. This suggests that if reflux is introduced to a non-azeotropic system in order to reject impurities from the overhead vapor, the lactic acid will also be rejected from the overhead vapor, which makes obtaining highly purified lactic acid using this method difficult.

EXAMPLE 17
Simulation of Lactic Acid Azeotropic Distillation with Low Reflux An ASPEN simulation was performed using the same apparatus and conditions as in Example 15, but with an azeotroping agent. The vapor-liquid-liquid equilibrium thermodynamic model for the dodecane—water—lactic acid system was based on UNIQUAC. The parameters for the UNIQUAC model were derived from UNIFAC at 50° C. and 150° C. Component vapor pressures used were as in examples 15 and 16.

In the simulation a molar flowrate of dodecane azeotroping agent of 267 lbmol/hr was used, which is identical to the molar flowrate of nitrogen non-azeotroping agent of 267 lbmol/hr used for examples 15 and 16. The dodecane vapor was at 158° C. and 200 mm Hg. The reflux was low and comparable to that in Example 15. It was predicted that 5539 lb/hr lactic acid would be carried overhead with an overhead temperature of 140.6° C. The total overhead vapor flowrate was 33993 lb/hr. Lactic acid was predicted to be 16.3% w/w of vapor stream.

EXAMPLE 18
Simulation of Lactic Acid Azeotropic Distillation with High Reflux An ASPEN simulation was performed using the same apparatus and conditions as in Example 16, but with an azeotroping agent. The vapor-liquid-liquid equilibrium thermodynamic model was the same as in Example 17. The vapor pressure data was the same as used in Examples 15, 16, and 17. The simulation included 267 lbmol/hr dodecane vapor at 158° C. and 200 mmHg. The reflux was relatively high and comparable to that in Example 16. It was predicted that 5077 lb/hr lactic acid would be carried overhead with a total of 30314 lb/hr overhead vapor. Lactic acid was predicted to be 16.8% w/w of the vapor stream.

The relatively higher reflux in Example 18 has little effect on the lactic acid recovery, as compared to recovery of lactic acid in Example 17, which had relatively lower reflux. Reflux can be used to reject other heavy species. Reflux can actually act to increase the lactic acid concentration in the overhead vapor comprising the lactic acid—dodecane azeotrope.

EXAMPLE 19
Simulation of Lactic Acid Azeotropic Distillation with Reflux

An ASPEN simulation was performed using the same apparatus and conditions as in Example 18, with the exception that the flowrate of the dodecane azeotroping agent was lowered to only 44.0 lbmol/hr. Excellent removal of acetic acid impurity was predicted, indicating the method could be used to remove volatile acids (or other light species) from aqueous lactic acid. In practice, some of the acetic acid could be present in a feed stream as the ester species lactoylacetate.

EXAMPLE 20
One Column Distillation

A cation exchange treated dilute aqueous solution of 41.18% w/w lactic acid with an optical purity of 99.70% containing 228.9 mmole of lactic acid was fed continuously to the top of a vacuum jacket glass distillation column containing five (5) cross-flow bubble plates similar to those found in large industrial tray distillation columns. A countercurrent flow of n-dodecane vapor was introduced in the bottom of the column. The system was operated at a reduced pressure of 23.2 inches Hg vacuum. A stream of dodecane vapor was generated from a boiling pot at the bottom of the column at a temperature of 161.5° C. to 162.9° C. The top of the column averaged 130° C. Two overhead fractions were collected during the course of the feed containing a total of 1428 mmole of 1-dodecane vapor and 209.1 mmole of lactic acid monomer, representing a recovery of 87.4% of the monomer lactic acid present in the feed. Two fractions collected from the overhead were analyzed for D-lactic acid by enzymatic assay. Total D-lactic acid and L-lactic acid was analyzed by HPLC. The overhead samples were found to be 99.95 and 99.93% optically pure. This example teaches that the azeotropic distillation process can be performed in a small version of industrial tray columns. Earlier examples used packed columns. In none of these examples was wiped film or short path distillation equipment necessary to obtain high yields of lactic acid.

EXAMPLE 21
Two Distillation Columns in Series

Two packed fractional distillation columns were connected in series. The overhead vapor product from the first column was used to feed the middle of the second column. Both columns were packed with a total height of about 6 inches stainless steel mesh packing. Column 1 had 2" of upper section packing above the liquid fermentation broth feed location and 4" of lower packing below the feed location. Column 2 had 2" of upper section packing above the liquid fermentation broth feed location and 4" of lower packing below the feed location.

A crude aqueous lactic acid solution, derived from fermentation of a mixture of glucose, maltose and other sugars and containing various fermentation impurities that had been treated by ion exchange and concentrated by evaporation and that included impurities such as acetic acid and glycerol, was fed to location near the middle of the first distillation column. Dodecane was fed to the bottom of the first distillation column and vaporized.

At the end of the continuous feed distillation operation, the overhead samples from the second column were separated into two phases: the light phase contained mainly dodecane, while the heavy phase contained mainly water and light acid impurities including a substantial portion of the feed acetic acid as well as other light impurities. The bottoms from the first column separated into two phases: the light phase was substantially dodecane while the heavy phase was a viscous material that contained residual sugars and glycerol. The bottoms from the second column contained 87% of the total lactic acid values fed to the system during the experiment and was largely free of both light impurities and heavy impurities and analysis by HPLC showed quality comparable to commercially available lactic acid.

This example teaches that fractional distillation can be used in conjunction with the invention here to obtain a high purity material.

All of the methods disclosed and claimed herein can be made and executed without undue experimentation in light of the present disclosure. While the methods of this invention have been described in terms of preferred embodiments, it will be apparent to those of skill in the art that variations may be applied to the methods and in the steps or in the sequence of steps of the methods described herein without departing from the concept, spirit and scope of the invention. More specifically, it will be apparent that certain agents which are both chemically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. An azeotropic distillation process for the recovery of at least one of an organic acid or an organic acid amide from a feed stream comprising at least one of the organic acid or the organic acid amide, comprising the steps of:
    mixing at least one azeotroping agent and a feed stream that comprises at least one of an organic acid or an organic acid amide and water, wherein the organic acid is selected from the group consisting of monocarboxylic acids, dicarboxylic acids, and tricarboxylic acids having from 2 to 8 carbon atoms, and the organic acid amide is selected from the group consisting of amides of monocarboxylic acids, dicarboxylic acids, and tricarboxylic acids having from 2 to 8 carbon atoms; and
    distilling the mixture comprising the at least one azeotroping agent and the feed stream by a method comprising the steps of
        (i) heating the mixture, wherein the heating is sufficient to produce a first vapor stream that comprises water and at least one first heteroazeotrope comprising (a) the organic acid or the organic acid amide and (b) the at least one azeotroping agent; and
        (ii) separating the first vapor stream from the mixture and producing a first bottoms stream, wherein the first bottoms stream comprises at least some of the organic acid or the organic acid amide, wherein the first bottoms stream is capable of being separated into a first phase and a second phase, wherein the first phase comprises a higher concentration of the organic acid or the organic acid amide than the second phase, and wherein the second phase comprises the at least one azeotroping agent;
    separating the first bottoms stream into a first phase and a second phase;
    condensing the first vapor stream to produce a first liquid stream;
    distilling the first liquid stream by a method comprising the steps of
        (A) adjusting the temperature of the first liquid stream to a temperature sufficient to produce a second vapor stream that comprises an azeotrope that comprises water and the at least one azeotroping agent and a second bottoms stream;
        (B) separating the second vapor stream from the second bottoms stream, wherein the second bottoms stream comprises at least some of the organic acid or the organic acid amide.

2. The process of claim 1, further comprising recovering at least some of the organic acid or the organic acid amide by separating the first phase from the second phase.

3. The process of claim 2, wherein recovered organic acid is heat stable.

4. The process of claim 2, wherein the recovered organic acid or organic acid amide is an alpha hydroxy acid or amide that is at least 98% optically pure.

5. The process of claim 2, wherein the feed stream further comprises at least one impurity, and wherein the at least one impurity is at a lower concentration in the organic acid recovered from the separated first phase than in the feed stream.

6. The process of claim 1, wherein a vacuum is used in separating the first vapor stream from the mixture.

7. The process of claim 1, wherein the at least one heteroazeotrope further comprises water.

8. The process of claim 1, wherein the process is a continuous process.

9. The process of claim 1, wherein the process is a batch process.

10. The process of claim 1, wherein the at least one azeotroping agent that is mixed with the feed stream as a vapor.

11. The process of claim 1, wherein the at least one azeotroping agent and the feed stream are mixed with one another in a column.

12. The process of claim 1, wherein the at least one azeotroping agent and the feed stream are mixed with one another in a flash reactor.

13. The process of claim 1, wherein the mixing of the at least one azeotroping agent and the feed stream is countercurrent.

14. The process of claim 1, wherein the process is performed at atmospheric pressure.

15. The process of claim 1, wherein the feed stream comprises a fermentation broth that has been thermally treated.

16. An azeotropic distillation process for the recovery of at least one of an organic acid or an organic acid amide from a feed stream comprising at least one of the organic acid or the organic acid amide, comprising the steps of:
    mixing at least one azeotroping agent and a feed stream that comprises at least one of an organic acid or an organic acid amide and water, wherein the organic acid is selected from the group consisting of monocarboxylic acids, dicarboxylic acids, and tricarboxylic acids having from 2 to 8 carbon atoms, and the organic acid amide is selected from the group consisting of amides of monocarboxylic acids, dicarboxylic acids, and tricarboxylic acids having from 2 to 8 carbon atoms; and
    distilling the mixture comprising the at least one azeotroping agent and the feed stream by a method comprising the steps of
        (i) heating the mixture, wherein the heating is sufficient to produce a first vapor stream that comprises water and at least one first heteroazeotrope comprising (a) the organic acid or the organic acid amide and (b) the at least one azeotroping agent; and (ii) separating the first vapor stream from the mixture and producing a first bottoms stream; and condensing the first vapor stream to form a first liquid stream, wherein the first liquid stream comprises at least some of the organic acid or the organic acid amide, wherein the first liquid stream is capable of being separated into a first phase and a second phase, wherein the first phase comprises a higher concentration of the organic acid or the organic acid amide than the second phase, and wherein the second phase comprises the at least one azeotroping agent, wherein the first liquid stream comprises a first phase having at least about 30 wt % water, and wherein the at least one azeotroping agent is capable of forming a second heteroazeotrope consisting of water and the at least one azeotroping agent, further comprising the step of distilling the first liquid stream by a method comprising the steps of (A) heating the first liquid stream to produce a second vapor stream and a second bottoms stream, wherein the second bottoms stream comprises at least some of the organic acid or the organic acid amide, and (B) separating the second vapor stream from the the second bottoms stream, wherein the second vapor stream comprises the second heteroazeotrope, and wherein the second bottoms stream is capable of being separated into a third phase and a fourth phase, wherein the third phase comprises a higher concentration of the organic acid or the organic acid amide than the fourth phase, and wherein the fourth phase comprises the at least one azeotroping agent.

17. The method of claim 16, further comprising separating the second bottoms stream into the third phase and the fourth phase.

18. The process of claim 16, further comprising recovering the organic acid or the organic acid amide by separating the third phase from the fourth phase.

19. The process of claim 18, wherein the recovered organic acid is heat stable.

20. The process of claim 18, wherein the recovered organic acid or amide is an alpha hydroxy acid or amide that is at least 98% optically pure.

21. The process of claim 18, wherein the feed stream comprises at least one impurity, and wherein the at least one impurity is at a lower concentration in the organic acid or the organic acid amide recovered from the separated third phase than in the feed stream.

22. An azeotropic distillation process for the recovery of at least one of an organic acid or an organic acid amide from a feed stream comprising at least one of the organic acid or the organic acid amide, comprising the steps of:

mixing at least one azeotroping agent and a feed stream that comprises at least one of an organic acid or an organic acid amide and water, wherein the organic acid is selected from the group consisting of monocarboxylic acids, dicarboxylic acids, and tricarboxylic acids having from 2 to 8 carbon atoms, and the organic acid amide is selected from the group consisting of amides of monocarboxylic acids, dicarboxylic acids, and tricarboxylic acids having from 2 to 8 carbon atoms; and distilling the mixture comprising the at least one azeotroping agent and the feed stream by a method comprising the steps of (i) heating the mixture, wherein the heating is sufficient to produce a first vapor stream that comprises water and at least one first heteroazeotrope comprising (a) the organic acid or the organic acid amide and (b) the at least one azeotroping agent; and (ii) separating the first vapor stream from the mixture and producing a first bottoms stream; and condensing the first vapor stream to form a first liquid stream, wherein the first liquid stream is capable of being separated into a first phase and a second phase, wherein the first phase comprises a higher concentration of the organic acid or the organic acid amide than the second phase, and wherein the second phase comprises the at least one azeotroping agent; wherein the organic acid is selected from the group consisting of lactic acid, pyruvic acid, beta-hydroxybutyric acid, glycolic acid, propionic acid, and acetic acid.

23. An azeotropic distillation process for the recovery of at least one of an organic acid or an organic acid amide from a feed stream comprising at least one of the organic acid or the organic acid amide, comprising the steps of:

mixing at least one azeotroping agent and a feed stream that comprises at least one of an organic acid or an organic acid amide and water, wherein the organic acid is selected from the group consisting of monocarboxylic acids, dicarboxylic acids, and tricarboxylic acids having from 2 to 8 carbon atoms, and the organic acid amide is selected from the group consisting of amides of monocarboxylic acids, dicarboxylic acids, and tricarboxylic acids having from 2 to 8 carbon atoms; and distilling the mixture comprising the at least one azeotroping agent and the feed stream by a method comprising the steps of (i) heating the mixture, wherein the heating is sufficient to produce a first vapor stream that comprises water and at least one first heteroazeotrope comprising (a) the organic acid or the organic acid amide and (b) the at least one azeotroping agent; and (ii) separating the first vapor stream from the mixture and producing a first bottoms stream; and condensing the first vapor stream to form a first liquid stream, wherein the first liquid stream is capable of being separated into a first phase and a second phase, wherein the first phase comprises a higher concentration of the organic acid or the organic acid amide than the second phase, and wherein the second phase comprises the at least one azeotroping agent; wherein the organic acid amide is selected from the group consisting of lactamide, pyruvamide, beta-hydroxybutyamide, propionamide, and acetamide.

24. An azeotropic distillation process for the recovery of at least one of an organic acid or an organic acid amide from a feed stream comprising at least one of the organic acid or the organic acid amide, comprising the steps of:

mixing at least one azeotroping agent and a feed stream that comprises at least one of an organic acid or an organic acid amide and water, wherein the organic acid is selected from the group consisting of monocarboxylic acids, dicarboxylic acids, and tricarboxylic acids having from 2 to 8 carbon atoms, and the organic acid amide is selected from the group consisting of amides of monocarboxylic acids, dicarboxylic acids, and tricarboxylic acids having from 2 to 8 carbon atoms; and distilling the mixture comprising the at least one azeotroping agent and the feed stream by a method comprising the steps of (i) heating the mixture, wherein the heating is sufficient to produce a first vapor stream that comprises water and at least one first heteroazeotrope comprising (a)

the organic acid or the organic acid amide and (b) the at least one azeotroping agent; and (ii) separating the first vapor stream from the mixture and producing a first bottoms stream; and condensing the first vapor stream to form a first liquid stream, wherein the first liquid stream is capable of being separated into a first phase and a second phase, wherein the first phase comprises a higher concentration of the organic acid or the organic acid amide than the second phase, and wherein the second phase comprises the at least one azeotroping agent; wherein the organic acid is a hydroxy acid.

25. The process of claim 24, wherein the hydroxy acid is lactic acid.

26. An azeotropic distillation process for the recovery of at least one of an organic acid or an organic acid amide from a feed stream comprising at least one of the organic acid or the organic acid amide, comprising the steps of:

mixing at least one azeotroping agent and a feed stream that comprises at least one of an organic acid or an organic acid amide and water, wherein the organic acid is selected from the group consisting of monocarboxylic acids, dicarboxylic acids, and tricarboxylic acids having from 2 to 8 carbon atoms, and the organic acid amide is selected from the group consisting of amides of monocarboxylic acids, dicarboxylic acids, and tricarboxylic acids having from 2 to 8 carbon atoms; and distilling the mixture comprising the at least one azeotroping agent and the feed stream by a method comprising the steps of (i) heating the mixture, wherein the heating is sufficient to produce a first vapor stream that comprises water and at least one first heteroazeotrope comprising (a) the organic acid or the organic acid amide and (b) the at least one azeotroping agent; and (ii) separating the first vapor stream from the mixture and producing a first bottoms stream; and condensing the first vapor stream to form a first liquid stream, wherein the first liquid stream is capable of being separated into a first phase and a second phase, wherein the first phase comprises a higher concentration of the organic acid or the organic acid amide than the second phase, and wherein the second phase comprises the at least one azeotroping agent; wherein the organic acid amide is a hydroxyamide.

27. The process of claim 26, wherein the organic acid amide is lactamide.

28. An azeotropic distillation process for the recovery of at least one of an organic acid or an organic acid snide from a feed stream comprising at least one of the organic acid or the organic acid amide, comprising the steps of:

mixing at least one azeotroping agent and a feed stream that comprises at least one of an organic acid or an organic acid amide and water, wherein the organic acid is selected from the group consisting of monocarboxylic acids, dicarboxylic acids, and tricarboxylic acids having from 2 to 8 carbon atoms, and the organic acid amide is selected from the group consisting of amides of monocarboxylic acids, dicarboxylic acids, and tricarboxylic acids having from 2 to 8 carbon atoms; and distilling the mixture comprising the at least one azeotroping agent and the feed steam by a method comprising the steps of (i) heating the mixture, wherein the heating is sufficient to produce a first vapor stream that comprises water and at least one first heteroazeotrope comprising (a) the organic acid or the organic acid amide and (b) the at least one azeotroping agent; and (ii) separating the first vapor stream from the mixture and producing a first bottoms stream; and condensing the first vapor stream so form a first liquid stream, wherein the first liquid stream is capable of being separated into a first phase and a second phase, wherein the first phase comprises a higher concentration of the organic acid or the organic acid amide than the second phase, and wherein the second phase comprises the at least one azeotroping agent; wherein the feed stream is a fermentation broth.

29. The process of claim 28, wherein the fermentation broth is concentrated.

30. The process of claim 28, wherein the fermentation broth is partially purified.

31. The process of claim 24, wherein the fermentation broth is de-cationized.

32. The process of claim 28, wherein the fermentation broth is acidified.

33. An azeotropic distillation process for the recovery of at least one of an organic acid or an organic acid amide from a feed stream comprising at least one of the organic acid or the organic acid amide, comprising the steps of:

mixing at least one azeotroping agent and a feed stream that comprises at least one of an organic acid or an organic acid amide and water, wherein the organic acid is selected from the group consisting of monocarboxylic acids, dicarboxylic acids, and tricarboxylic acids having from 2 to 8 carbon atoms, and the organic acid amide is selected from the group consisting of amides of monocarboxylic acids, dicarboxylic acids, and tricarboxylic acids having from 2 to 8 carbon atoms; and distilling the mixture comprising the at least one azeotroping agent and the feed stream by a method comprising the steps of (i) heating the mixture, wherein the heating is sufficient to produce a first vapor stream that comprises water and at least one first heteroazeotrope comprising (a) the organic acid or the organic acid amide and (b) the at least one azeotroping agent; and (ii) separating the first vapor stream from the mixture and producing a first bottoms stream; and condensing the first vapor stream to form a first liquid stream, wherein the first liquid stream is capable of being separated into a first phase and a second phase, wherein the first phase comprises a higher concentration of the organic acid or the organic acid amide than the second phase, and wherein the second phase comprises the at least one azeotroping agent; wherein the at least one azeotroping agent is a hydrocarbon having a boiling point of between about 100° C. less than and 150° C. more than the organic acid or the organic acid amide boiling point.

34. The process of claim 33, wherein the hydrocarbon has a boiling point of between about 50° C. less than and 50° C. more than the organic acid or the organic acid amide boiling point.

35. The process of claim 33, wherein the hydrocarbon has 7 to 16 carbon atoms.

36. The process of claim 35, wherein the hydrocarbon is selected from the group consisting of diethylbenzene, hexadecane, tetradecane, dodecane, decane, octylbenzene, and propylbenzene.

37. The process of claim 35, wherein the hydrocarbon is aromatic or aliphatic.

38. The process of claim 37, wherein the aliphatic hydrocarbon is branched, unbranched, or cyclic.

39. An azeotropic distillation process for the recovery of at least one of an organic acid or an organic acid amide from a feed stream comprising at least one of the organic acid or the organic acid amide, comprising the steps of:

mixing at least one azeotroping agent and a feed stream that comprises at least one of an organic acid or an organic acid amide and water, wherein the organic acid is selected from the group consisting of monocarboxylic acids, dicarboxylic acids, and tricarboxylic acids having from 2 to 8 carbon atoms, and the organic acid amide is selected from the group consisting of amides of monocarboxylic acids, dicarboxylic acids, and tricarboxylic acids having from 2 to 8 carbon atoms; and distilling the mixture comprising the at least one azeotroping agent and the feed stream by a method comprising the steps of
 (i) heating the mixture, wherein the heating is sufficient to produce a first vapor stream that comprises water and at least one first heteroazeotrope comprising (a) the organic acid or the organic acid amide and (b) the at least one azeotroping agent; and
 (ii) separating the first vapor stream from the mixture and producing a first bottoms stream; and condensing the first vapor stream to form a first liquid stream, wherein the first liquid stream is capable of being separated into a first phase and a second phase, wherein the first phase comprises a higher concentration of the organic acid or the organic acid amide than the second phase, and wherein the second phase comprises the at least one azeotroping agent; wherein the feed stream comprises between about 15 wt % to 85 wt % of the organic acid, and further comprises greater than about 10 wt % water, and between about 5 wt % to 70 wt % at least one salt of the organic acid.

40. The process of claim 39, wherein the at least one salt is selected from the group consisting of ammonium salts, sodium salts, potassium salts, and calcium salts of the organic acid.

41. An azeotropic distillation process for the recovery of at least one of an organic acid or an organic acid amide from a feed stream comprising at least one of the organic acid or the organic acid amide, comprising the steps of:

mixing at least one azeotroping agent and a feed stream that comprises at least one of an organic acid or an organic acid amide and water, wherein the organic acid is selected from the group consisting of monocarboxylic acids, dicarboxylic acids, and tricarboxylic acids having from 2 to 8 carbon atoms, and the organic acid amide is selected from the group consisting of amides of monocarboxylic acids, dicarboxylic acids, and tricarboxylic acids having from 2 to 8 carbon atoms; and distilling the mixture comprising the at least one azeotroping agent and the feed stream by a method comprising the steps of
 (i) heating the mixture, wherein the heating is sufficient to produce a first vapor stream that comprises water and at least one first heteroazeotrope comprising (a) the organic acid or the organic acid amide and (b) the at least one azeotroping agent; and
 (ii) separating the first vapor stream from the mixture and producing a first bottoms stream; and condensing the first vapor stream to form a first liquid stream, wherein the first liquid stream is capable of being separated into a first phase and a second phase, wherein the first phase comprises a higher concentration of the organic acid or the organic acid amide than the second phase, and wherein the second phase comprises the at least one azeotroping agent; wherein the feed stream comprises less than about 5 wt % salts, greater than about 15 wt % the organic acid, and at least one impurity.

42. The process of claim 41, wherein the at least one impurity is a compound selected from the group consisting of organic acids, proteins, carbohydrates, and alcohols.

43. The process of claim 42, wherein the feed stream initially comprises between about 5.1 wt % and 30 wt % water, further comprising the step of adding water to the feed stream sufficient to cause a shift in the volatility of the at least one impurity.

44. The process of claim 43, wherein added water alters the composition of the feed stream such that the feed stream comprises at least about 50 wt % water.

45. The process of claim 43, wherein water is added to the feed stream prior to heating the mixture comprising the feed stream and the at least one azeotroping agent.

46. The process of claim 43, wherein water is added to the mixture comprising the feed stream and the at least one azeotroping agent during heating the mixture.

47. The process of claim 46, wherein the first liquid stream resulting from heating the mixture prior to addition of water has a concentration of the at least one impurity that differs from concentration of the at least one impurity in the first liquid stream resulting from heating the mixture after addition of water.

48. An azeotropic distillation process for the recovery of at least one of an organic acid or an organic acid amide from a feed stream comprising at least one of the organic acid or the organic acid amide, comprising the steps of:

mixing at least one azeotroping agent and a feed stream that comprises at least one of an organic acid or an organic acid amide and water, wherein the organic acid is selected from the group consisting of monocarboxylic acids, dicarboxylic acids, and tricarboxylic acids having from 2 to 8 carbon atoms, and the organic acid amide is selected from the group consisting of amides of monocarboxylic acids, dicarboxylic acids, and tricarboxylic acids having from 2 to 8 carbon atoms; and distilling the mixture comprising the at least one azeotroping agent and the feed stream by a method comprising the steps of
 (i) heating the mixture, wherein the heating is sufficient to produce a first vapor stream that comprises water and at least one first heteroazeotrope comprising (a) the organic acid or the organic acid amide and (b) the least one azeotroping agent; and
 (ii) separating the first vapor stream from the mixture and producing a first bottoms stream; and wherein the first vapor stream comprises lactamide and lactic acid.

49. The process of claim 48 wherein the lactamide and the lactic acid of the first vapor stream are azeotropically distilled.

50. An azeotropic distillation process for the recovery of at least one of an organic acid or an organic acid amide from a feed stream comprising at least one of the organic acid or the organic acid amide, comprising the steps of:

mixing at least one azeotroping agent and a feed stream that comprises at least one of an organic acid or an organic acid amide and water, wherein the organic acid is selected from the group consisting of monocarboxylic acids, dicarboxylic acids, and tricarboxylic acids having from 2 to 8 carbon atoms, and the organic acid amide is selected from the group consisting of amides of monocarboxylic acids, dicarboxylic acids, and tricarboxylic acids having from 2 to 8 carbon atoms; and distilling the mixture comprising the at least one azeotroping agent and the feed stream by a method comprising the steps of
  (i) heating the mixture, wherein the heating is sufficient to produce a first vapor stream that comprises water and at least one first heteroazeotrope comprising (a) the organic acid or the organic acid amide and (b) the at least one azeotroping agent; and
  (ii) separating the first vapor stream from the mixture and producing a first bottoms stream; and wherein the at least one of an organic acid or an organic acid amide is the product of the treatment of a polyester.

51. An azeotropic distillation process for the recovery of at least one of an organic acid or an organic acid amide front a feed stream comprising at least one of the organic acid or the organic acid amide, comprising the steps of:

mixing at least one azeotroping agent and a feed stream that comprises at least one of an organic acid or an organic acid amide and water, wherein the organic acid is selected from the group consisting of monocarboxylic acids, dicarboxylic acids, and tricarboxylic acids having from 2 to 8 carbon atoms, and the organic acid amide is selected from the group consisting of amides of monocarboxylic acids, dicarboxylic acids, and tricarboxylic acids having from 2 to 8 carbon atoms; and distilling the mixture comprising the at least one azeotroping agent and the feed steam by a method comprising the steps of
  (i) heating the mixture, wherein the heating is sufficient to produce a first vapor stream that comprises water and at least one first heteroazeotrope comprising (a) the organic acid or the organic acid amide and (b) the at least one azeotroping agent; and
  (ii) separating the first vapor steam from the mixture and producing a first bottoms stream; and wherein the time the mixture is heated in step (i) is limited in order to reduce racemization.

52. The process of claim 51, wherein the at least one azeotroping agent is a linear or branched alkane having a normal boiling point between about 150° C. and 270° C.

53. An azeotropic distillation process for the recovery of at least one of an organic acid or an organic acid amide from a feed stream comprising at least one of the organic acid or the organic acid amide, comprising the steps of:

mixing at least one azeotroping agent and a feed stream that comprises at least one of an organic acid or an organic acid amide and water, wherein the organic acid is selected from the group consisting of monocarboxylic acids, dicarboxylic acids, and tricarboxylic acids having from 2 to 8 carbon atoms, and the organic acid amide is selected from the group consisting of amides of monocarboxylic acids, dicarboxylic acids, and tricarboxylic acids having from 2 to 8 carbon atoms; and distilling the mixture comprising the at least one azeotroping agent and the feed stream by a method comprising the steps of
  (i) heating the mixture, wherein the heating is sufficient to produce a first vapor stream that comprises water and at least one first heteroazeotrope comprising (a) the organic acid or the organic acid amide and (b) the at least one azeotroping agent; and
  (ii) separating the first vapor stream from the mixture and producing a first bottoms stream, wherein the first bottoms stream comprises as least some of the organic acid or the organic acid amide, wherein the first bottoms stream is capable of being separated into a first phase and a second phase, wherein the first phase comprises a higher concentration of the organic acid or the organic acid amide than the second phase, and wherein the second phase comprises the at least one azeotroping agent;
  separating the first bottoms stream into a first phase and a second phase;
  condensing the first vapor stream to produce a first liquid stream;
  distilling the first liquid stream by a method comprising the steps of
    (A) adjusting the temperature of the first liquid stream to a temperature sufficient to produce a second vapor stream that comprises an azeotrope that comprises water and the at least one azeotroping agent and a second bottoms stream;
    (B) separating the second vapor stream from the second bottoms stream, wherein the second bottoms stream comprises at least some of the organic acid or the organic acid amide; and
  wherein the mixing is done in a first fractional distillation column, the separating step (B) is done in a second fractional distillation column, and wherein the first fractional distillation column and the second fractional distillation column are used in series.

54. The process of claim 53, wherein the second bottoms stream is separated into a third phase and a fourth phase, wherein the third phase comprises a higher concentration of the organic acid or the organic acid amide than the fourth phase and azeotroping agent, and the third phase is treated with a steam stripper to remove at least some azeotroping agent.

55. The process of claim 53, wherein the at least one azeotroping agent comprises greater than about 99% of a single hydrocarbon.

56. An azeotropic distillation process for the recovery of at least one of an organic acid or an organic acid amide from a feed stream comprising at least one of the organic acid or the organic acid amide, comprising the steps of:

mixing at least one azeotroping agent and a feed stream that comprises at least one of an organic acid or an organic acid amide and water, wherein the organic acid is selected from the group consisting of monocarboxylic acids, dicarboxylic acids, and tricarboxylic acids having from 2 to 8 carbon atoms, and the organic acid amide is selected from the group consisting of amides of monocarboxylic acids, dicarboxylic acids, and tricarboxylic acids having from 2 to 8 carbon atoms; and distilling the mixture comprising the at least one azeotroping agent and the feed stream by a method comprising the steps of
  (i) heating the mixture, wherein the heating is sufficient to produce a fast vapor stream that comprises water and at least one first heteroazeotrope comprising (a) the organic acid or the organic acid amide and (b) the at least one azeotroping agent; and
  (ii) separating the first vapor stream from the mixture and producing a first bottoms stream; and
  wherein the at least one azeotroping agent is a long chain alcohol having 7 to 13 carbon atoms, and the organic acid is lactic acid.

57. An azeotropic distillation process for the recovery of at least one of an organic acid or an organic acid amide from a feed steam comprising at least one of the organic acid or the organic acid amide, comprising the steps of, mixing at least one azeotroping agent and a feed steam that comprises at least one of an organic acid or an organic acid amide and water, wherein the organic acid is selected from the group consisting of monocarboxylic acids, dicarboxylic acids, and tricarboxylic acids having from 2 to 8 carbon atoms, and the organic acid amide is selected from the group consisting of amides of monocarboxylic acids, dicarboxylic acids, and tricarboxylic acids having from 2 to 8 carbon atoms; and distilling the mixture comprising the at least one azeotroping agent and the feed stream by a method comprising the steps of
  (i) heating at the mixture, wherein the heating is sufficient to produce a first vapor stream that comprises water and at least one first heteroazeotrope comprising (a) the organic acid or the organic acid amide and (b) the at least one azeotroping agent; and
  (ii) separating the first vapor stream from the mixture and producing a first bottoms stream; and wherein the at least one azeotroping agent is an aromatic hydrocarbon having 9 to 15 carbon atoms and the organic acid is lactic acid.

58. An azeotropic distillation process for the recovery of at least one of an organic acid or an organic acid amide from a feed stream comprising at least one of the organic acid or the organic acid amide, comprising the steps of:

mixing at least one azeotroping agent and a feed stream that comprises at least one of an organic acid or an organic acid amide and water, wherein the organic acid is selected from the group consisting of monocarboxylic acids, dicarboxylic acids, and tricarboxylic acids having from 2 to 8 carbon atoms, and the organic acid amide is selected from the group consisting of amides of monocarboxylic acids, dicarboxylic acids, and tricarboxylic acids having from 2 to 8 carbon atoms; and distilling the mixture comprising the at least one azeotroping agent and the feed stream by a method comprising the steps of
  (i) heating the mixture, wherein the heating is sufficient to produce a first vapor stream that comprises water and at least one first heteroazeotrope comprising (a) the organic acid or the organic acid amide and (b) the at least one azeotroping agent; and
  (ii) separating the first vapor stream from the mixture and producing a first bottoms stream; and condensing the first vapor stream to form a first liquid stream, wherein the first liquid stream is capable of being separated into a first phase and a second phase, wherein the first phase comprises a higher concentration of the organic acid or the organic acid amide than the second phase, and wherein the second phase comprises the at least one azeotroping agent; wherein the at least one azeotroping agent is an ether having from 7 to 16 carbon atoms or an alcohol having from 7 to 13 carbon atoms.

* * * * *

UNITED STATES PATENT AND TRADEMARK OFFICE
CERTIFICATE OF CORRECTION

| | | |
|---|---|---|
| PATENT NO. | : 6,982,026 B2 | |
| APPLICATION NO. | : 09/809649 | |
| DATED | : January 3, 2006 | |
| INVENTOR(S) | : Michael Charles Milner Cockrem and Istvan Kovacs | |

It is certified that error appears in the above-identified patent and that said Letters Patent is hereby corrected as shown below:

Column 36,
Line 40, delete "wherein the mixing of the at least one azeotroping agent" and insert -- wherein the at least one mixing of the azeotroping agent --.

Column 37,
Line 23, delete the third instance of "the".

Column 37, Line 48 through Column 38, line 14,
Delete the following:

"22. An azeotropic distillation process for the recovery of at least one of an organic acid or an organic acid amide from a feed stream comprising at least one of the organic acid or the organic acid amide, comprising the steps of:
  mixing at least one azeotroping agent and a feed stream that comprises at least one of an organic acid or an organic acid amide and water, wherein the organic acid is selected from the group consisting of monocarboxylic acids, dicarboxylic acids, and tricarboxylic acids having from 2 to 8 carbon atoms, and the organic acid amide is selected from the group consisting of amides of monocarboxylic acids, dicarboxylic acids, and tricarboxylic acids having from 2 to 8 carbon atoms; and
  distilling the mixture comprising the at least one azeotroping agent and the feed stream by a method comprising the steps of
    (i) heating the mixture, wherein the heating is sufficient to produce a first vapor stream that comprises water and at least one first heteroazeotrope comprising (a) the organic acid or the organic acid amide and (b) the at least one azeotroping agent; and
    (ii) separating the first vapor stream from the mixture and producing a first bottoms stream; and
  condensing the first vapor stream to form a first liquid stream, wherein the first liquid stream is capable of being separated into a first phase and a second phase, wherein the first phase comprises a higher concentration of the organic acid or the organic acid amide than the second phase, and wherein the second phase comprises the at least one azeotroping agent; wherein the organic acid is selected from the group consisting of lactic acid, pyruvic acid, beta-hydroxybutyric acid, glycolic acid, propionic acid, and acetic acid."

and insert the following:
-- 22. The process of claim 1, wherein the organic acid is selected from the group consisting of lactic acid, pyruvic acid, beta-hydroxybutyric acid, glycolic acid, propionic acid, and acetic acid. --

UNITED STATES PATENT AND TRADEMARK OFFICE
CERTIFICATE OF CORRECTION

PATENT NO. : 6,982,026 B2
APPLICATION NO. : 09/809649
DATED : January 3, 2006
INVENTOR(S) : Michael Charles Milner Cockrem and Istvan Kovacs It is certified that error appears in the above-identified patent and that said Letters Patent is hereby corrected as shown below:

Column 38,
Lines 15-47, delete the following:

"23. An azeotropic distillation process for the recovery of at least one of an organic acid or an organic acid amide from a feed stream comprising at least one of the organic acid or the organic acid amide, comprising the steps of:
  mixing at least one azeotroping agent and a feed stream that comprises at least one of an organic acid or an organic acid amide and water, wherein the organic acid is selected from the group consisting of monocarboxylic acids, dicarboxylic acids, and tricarboxylic acids having from 2 to 8 carbon atoms, and the organic acid amide is selected from the group consisting of amides of monocarboxylic acids, dicarboxylic acids, and tricarboxylic acids having from 2 to 8 carbon atoms; and
distilling the mixture comprising the at least one azeotroping agent and the feed stream by a method comprising the steps of
  (i) heating the mixture, wherein the heating is sufficient to produce a first vapor stream that comprises water and at least one first heteroazeotrope comprising (a) the organic acid or the organic acid amide and (b) the at least one azeotroping agent; and
  (ii) separating the first vapor stream from the mixture and producing a first bottoms stream; and
condensing the first vapor stream to form a first liquid stream, wherein the first liquid stream is capable of being separated into a first phase and a second phase, wherein the first phase comprises a higher concentration of the organic acid or the organic acid amide than the second phase, and wherein the second phase comprises the at least one azeotroping agent; wherein the organic acid amide is selected from the group consisting of lactamide, pyruvamide, beta-hydroxybutyamide, propionamide, and acetamide."

Column 38, line 48 through Column 39, line 12,
Delete the following:

"24. An azeotropic distillation process for the recovery of at least one of an organic acid or an organic acid amide from a feed stream comprising at least one of the organic acid or the organic acid amide, comprising the steps of:
mixing at least one azeotroping agent and a feed stream that comprises at least one of an organic acid or an organic acid amide and water, wherein the organic acid is selected from the group consisting of monocarboxylic acids, dicarboxylic acids, and tricarboxylic acids having from 2 to 8 carbon atoms, and the organic acid amide is selected from the group consisting of amides of monocarboxylic acids, dicarboxylic acids, and tricarboxylic acids having from 2 to 8 carbon atoms; and
distilling the mixture comprising the at least one azeotroping agent and the feed stream by a method comprising the steps of
  (i) heating the mixture, wherein the heating is sufficient to produce a first vapor stream that comprises water and at least one first heteroazeotrope comprising (a) the organic acid or the organic acid amide and (b) the at least

UNITED STATES PATENT AND TRADEMARK OFFICE
CERTIFICATE OF CORRECTION

PATENT NO. : 6,982,026 B2
APPLICATION NO. : 09/809649
DATED : January 3, 2006
INVENTOR(S) : Michael Charles Milner Cockrem and Istvan Kovacs It is certified that error appears in the above-identified patent and that said Letters Patent is hereby corrected as shown below:

Column 38, line 48 through Column 39, line 12 (cont'd), one azeotroping agent; and
(ii) separating the first vapor stream from the mixture and producing a first bottoms stream; and
condensing the first vapor stream to form a first liquid stream, wherein the first liquid stream is capable of being separated into a first phase and a second phase, wherein the first phase comprises a higher concentration of the organic acid or the organic acid amide than the second phase, and wherein the second phase comprises the at least one azeotroping agent; wherein the organic acid is a hydroxy acid."

and insert the following:
-- 24. The process of claim 1, wherein the first phase comprises a higher concentration of the organic acid or the organic acid amide than the second phase, and wherein the second phase comprises the at least one azeotroping agent; wherein the organic acid is a hydroxy acid. --.

Column 39,
Line 39, delete "capable of".
Line 45, delete "a hydroxyamide" and insert -- lactamide --.
Lines 46-47, delete the following:
"27. The process of claim 26, wherein the organic acid amide is lactamide.".
Line 49, delete "snide" and insert -- amide --.

Column 40,
Line 5, delete "so" and insert -- to --.
Line 6, after "stream is" delete "capable of being".
Line 12, after "fermentation broth" insert -- , and wherein the fermentation broth is acidified --.
Lines 13-14, delete the following:
"29. The process of claim 28, wherein the fermentation broth is concentrated.".
Lines 15-16, delete the following:
"30. The process of claim 28, wherein the fermentation broth is partially purified.".
Lines 17-18, delete the following:
"31. The process of claim 24, wherein the fermentation broth is de-cationized.".
Lines 19-20, delete the following:
"32. The process of claim 28, wherein the fermentation broth is acidified.".

UNITED STATES PATENT AND TRADEMARK OFFICE
CERTIFICATE OF CORRECTION

PATENT NO. : 6,982,026 B2
APPLICATION NO. : 09/809649
DATED : January 3, 2006
INVENTOR(S) : Michael Charles Milner Cockrem and Istvan Kovacs It is certified that error appears in the above-identified patent and that said Letters Patent is hereby corrected as shown below:

Column 40 (cont'd),
Lines 21-54, delete the following:

"33. An azeotropic distillation process for the recovery of at least one of an organic acid or an organic acid amide from a feed stream comprising at least one of the organic acid or the organic acid amide, comprising the steps of:
  mixing at least one azeotroping agent and a feed stream that comprises at least one of an organic acid or an organic acid amide and water, wherein the organic acid is selected from the group consisting of monocarboxylic acids, dicarboxylic acids, and tricarboxylic acids having from 2 to 8 carbon atoms, and the organic acid amide is selected from the group consisting of amides of monocarboxylic acids, dicarboxylic acids, and tricarboxylic acids having from 2 to 8 carbon atoms; and
  distilling the mixture comprising the at least one azeotroping agent and the feed stream by a method comprising the steps of
    (i) heating the mixture, wherein the heating is sufficient to produce a first vapor stream that comprises water and at least one first heteroazeotrope comprising (a) the organic acid or the organic acid amide and (b) the at least one azeotroping agent; and
    (ii) separating the first vapor stream from the mixture and producing a first bottoms stream; and
  condensing the first vapor stream to form a first liquid stream, wherein the first liquid stream is capable of being separated into a first phase and a second phase, wherein the first phase comprises a higher concentration of the organic acid or the organic acid amide than the second phase, and wherein the second phase comprises the at least one azeotroping agent; wherein the at least one azeotroping agent is a hydrocarbon having a boiling point of between about 100° C. less than and 150° C. more than the organic acid or the organic acid amide boiling point."

and insert the following:
-- 33. The process of claim 1, wherein the at least one azeotroping agent is a hydrocarbon having a boiling point of between about 100 °C less than and 150 °C more than the organic acid or the organic acid amide boiling point. --.

Column 41,
Lines 1-34, delete the following:

"39. An azeotropic distillation process for the recovery of at least one of an organic acid or an organic acid amide from a feed stream comprising at least one of the organic acid or the organic acid amide, comprising the steps of:
  mixing at least one azeotroping agent and a feed stream that comprises at least one of an organic acid or an organic acid amide and water, wherein the organic acid is selected from the group consisting of monocarboxylic acids, dicarboxylic acids, and tricarboxylic acids having from 2 to 8 carbon atoms, and the organic acid amide is selected from the group consisting of amides of monocarboxylic acids, dicarboxylic acids, and tricarboxylic acids having from 2 to 8 carbon

UNITED STATES PATENT AND TRADEMARK OFFICE
CERTIFICATE OF CORRECTION

PATENT NO. : 6,982,026 B2
APPLICATION NO. : 09/809649
DATED : January 3, 2006
INVENTOR(S) : Michael Charles Milner Cockrem and Istvan Kovacs It is certified that error appears in the above-identified patent and that said Letters Patent is hereby corrected as shown below:

Column 41 (cont'd), atoms; and
  distilling the mixture comprising the at least one azeotroping agent and the feed stream by a method comprising the steps of
    (i) heating the mixture, wherein the heating is sufficient to produce a first vapor stream that comprises water and at least one first heteroazeotrope comprising (a) the organic acid or the organic acid amide and (b) the at least one azeotroping agent; and
    (ii) separating the first vapor stream from the mixture and producing a first bottoms stream; and condensing the first vapor stream to form a first liquid stream, wherein the first liquid stream is capable of being separated into a first phase and a second phase, wherein the first phase comprises a higher concentration of the organic acid or the organic acid amide than the second phase, and wherein the second phase comprises the at least one azeotroping agent; wherein the feed stream comprises between about 15 wt % to 85 wt % of the organic acid, and further comprises greater than about 10 wt % water, and between about 5 wt % to 70 wt % at least one salt of the organic acid."

and insert the following:
-- 39. The process of claim 1, wherein the feed stream comprises between about 15 wt% to 85 wt% of the organic acid, and further comprises greater than about 10 wt% water, and between about 5 wt% to 70 wt% at least one salt of the organic acid. --.

Column 41, line 39 through Column 42, line 5,
Delete the following:

"41. An azeotropic distillation process for the recovery of at least one of an organic acid or an organic acid amide from a feed stream comprising at least one of the organic acid or the organic acid amide, comprising the steps of:
  mixing at least one azeotroping agent and a feed stream that comprises at least one of an organic acid or an organic acid amide and water, wherein the organic acid is selected from the group consisting of monocarboxylic acids, dicarboxylic acids, and tricarboxylic acids having from 2 to 8 carbon atoms, and the organic acid amide is selected from the group consisting of amides of monocarboxylic acids, dicarboxylic acids, and tricarboxylic acids having from 2 to 8 carbon atoms; and
  distilling the mixture comprising the at least one azeotroping agent and the feed stream by a method comprising the steps of
    (i) heating the mixture, wherein the heating is sufficient to produce a first vapor stream that comprises water and at least one first heteroazeotrope comprising (a) the organic acid or the organic acid amide and (b) the at least one azeotroping agent; and
    (ii) separating the first vapor stream from the mixture and producing a first bottoms stream; and

UNITED STATES PATENT AND TRADEMARK OFFICE
CERTIFICATE OF CORRECTION

PATENT NO. : 6,982,026 B2
APPLICATION NO. : 09/809649
DATED : January 3, 2006
INVENTOR(S) : Michael Charles Milner Cockrem and Istvan Kovacs It is certified that error appears in the above-identified patent and that said Letters Patent is hereby corrected as shown below:

Column 41, line 39 through Column 42, line 5 (cont'd),

> condensing the first vapor stream to form a first liquid stream, wherein the first liquid stream is capable of being separated into a first phase and a second phase, wherein the first phase comprises a higher concentration of the organic acid or the organic acid amide than the second phase, and wherein the second phase comprises the at least one azeotroping agent; wherein the feed stream comprises less than about 5 wt % salts, greater than about 15 wt % the organic acid, and at least one impurity."

and insert the following:
-- 41. The process of claim 1, wherein the feed stream comprises less than about 5 wt% salts, greater than about 15 wt% the organic acid, and at least one impurity. --.

Column 42,
Line 51, after "first bottoms stream;" delete "and".
Line 53, after "acid" insert -- and wherein the lactamide and the lactic acid of the first vapor stream are azeotropically distilled --.
Lines 54-56, delete the following:
"49. The process of claim 48 wherein the lactamide and the lactic acid of the first vapor stream are azeotropically distilled.".

Column 42, line 57 through Column 43, line 14,
Delete the following:

> "50. An azeotropic distillation process for the recovery of at least one of an organic acid or an organic acid amide from a feed stream comprising at least one of the organic acid or the organic acid amide, comprising the steps of:
> mixing at least one azeotroping agent and a feed stream that comprises at least one of an organic acid or an organic acid amide and water, wherein the organic acid is selected from the group consisting of monocarboxylic acids, dicarboxylic acids, and tricarboxylic acids having from 2 to 8 carbon atoms, and the organic acid amide is selected from the group consisting of amides of monocarboxylic acids, dicarboxylic acids, and tricarboxylic acids having from 2 to 8 carbon atoms; and
> distilling the mixture comprising the at least one azeotroping agent and the feed stream by a method comprising the steps of
> (i) heating the mixture, wherein the heating is sufficient to produce a first vapor stream that comprises water and at least one first heteroazeotrope comprising (a) the organic acid or the organic acid amide and (b) the at least one azeotroping agent; and
> (ii) separating the first vapor stream from the mixture and producing a first bottoms stream; and wherein the at least one of an organic acid or an organic acid amide is the product of the treatment of a polyester."

UNITED STATES PATENT AND TRADEMARK OFFICE
CERTIFICATE OF CORRECTION

| | |
|---|---|
| PATENT NO. | : 6,982,026 B2 |
| APPLICATION NO. | : 09/809649 |
| DATED | : January 3, 2006 |
| INVENTOR(S) | : Michael Charles Milner Cockrem and Istvan Kovacs |

It is certified that error appears in the above-identified patent and that said Letters Patent is hereby corrected as shown below:

Column 42, line 57 through Column 43, line 14 (cont'd),
and insert the following:
-- 50. The process of claim 1, wherein the at least one of an organic acid or an organic acid amide is the product of the treatment of a polyester. --.

Column 43,
Line 16, delete "front" and insert -- from --.
Line 40, delete "claim 51" and insert -- claim 1 --.

Column 44,
Lines 38-63, delete the following:

"56. An azeotropic distillation process for the recovery of at least one of an organic acid or an organic acid amide from a feed stream comprising at least one of the organic acid or the organic acid amide, comprising the steps of:
   mixing at least one azeotroping agent and a feed stream that comprises at least one of an organic acid or an organic acid amide and water, wherein the organic acid is selected from the group consisting of monocarboxylic acids, dicarboxylic acids, and tricarboxylic acids having from 2 to 8 carbon atoms, and the organic acid amide is selected from the group consisting of amides of monocarboxylic acids, dicarboxylic acids, and tricarboxylic acids having from 2 to 8 carbon atoms; and
   distilling the mixture comprising the at least one azeotroping agent and the feed stream by a method comprising the steps of
      (i) heating the mixture, wherein the heating is sufficient to produce a fast vapor stream that comprises water and at least one first heteroazeotrope comprising (a) the organic acid or the organic acid amide and (b) the at least one azeotroping agent; and
      (ii) separating the first vapor stream from the mixture and producing a first bottoms stream; and
   wherein the at least one azeotroping agent is a long chain alcohol having 7 to 13 carbon atoms, and the organic acid is lactic acid."

and insert the following:
-- 56. The process of claim 1, wherein the at least one azeotroping agent is a long chain alcohol having 7 to 13 carbon atoms, and the organic acid is lactic acid. --.

Column 44, line 64 through Column 45, line 22,
Delete the following:

"57. An azeotropic distillation process for the recovery of at least one of an organic acid or an organic acid amide from a feed steam comprising at least one of the organic acid or the organic acid amide, comprising the steps of,
   mixing at least one azeotroping agent and a feed steam that comprises at least one of an organic acid or an organic acid amide and water, wherein the organic acid is selected from the group consisting of monocarboxylic acids, dicarboxylic acids, and tricarboxylic acids having from 2 to 8 carbon atoms, and the organic acid

UNITED STATES PATENT AND TRADEMARK OFFICE
CERTIFICATE OF CORRECTION

PATENT NO. : 6,982,026 B2
APPLICATION NO. : 09/809649
DATED : January 3, 2006
INVENTOR(S) : Michael Charles Milner Cockrem and Istvan Kovacs It is certified that error appears in the above-identified patent and that said Letters Patent is hereby corrected as shown below:

Column 44, line 64 through Column 45, line 22 (cont'd),

> amide is selected from the group consisting of amides of monocarboxylic acids, dicarboxylic acids, and tricarboxylic acids having from 2 to 8 carbon atoms; and
> distilling the mixture comprising the at least one azeotroping agent and the feed stream by a method comprising the steps of
> > (i) heating at the mixture, wherein the heating is sufficient to produce a first vapor stream that comprises water and at least one first heteroazeotrope comprising (a) the organic acid or the organic acid amide and (b) the at least one azeotroping agent; and
> > (ii) separating the first vapor stream from the mixture and producing a first bottoms stream; and and insert the following:
-- 57. The process of claim 1, wherein the at least one azeotroping agent is an aromatic hydrocarbon having 9 to 15 carbon atoms and the organic acid is lactic acid. --.

Column 45, line 23 through Column 46, line 26,
Delete the following:

> "58. An azeotropic distillation process for the recovery of at least one of an organic acid or an organic acid amide from a feed stream comprising at least one of the organic acid or the organic acid amide, comprising the steps of:
> > mixing at least one azeotroping agent and a feed stream that comprises at least one of an organic acid or an organic acid amide and water, wherein the organic acid is selected from the group consisting of monocarboxylic acids, dicarboxylic acids, and tricarboxylic acids having from 2 to 8 carbon atoms, and the organic acid amide is selected from the group consisting of amides of monocarboxylic acids, dicarboxylic acids, and tricarboxylic acids having from 2 to 8 carbon atoms; and
> > distilling the mixture comprising the at least one azeotroping agent and the feed stream by a method comprising the steps of
> > > (i) heating the mixture, wherein the heating is sufficient to produce a first vapor stream that comprises water and at least one first heteroazeotrope comprising (a) the organic acid or the organic acid amide and (b) the at least one azeotroping agent; and
> > > (ii) separating the first vapor stream from the mixture and producing a first bottoms stream; and
> > condensing the first vapor stream to form a first liquid stream, wherein the first liquid stream is capable of being separated into a first phase and a second phase, wherein the first phase comprises a higher concentration of the organic acid or the organic acid amide than the second phase, and wherein the second phase comprises the at least one azeotroping agent; wherein the at least one azeotroping agent is an ether having from 7 to 16 carbon atoms or an alcohol having from 7 to 13 carbon atoms."

UNITED STATES PATENT AND TRADEMARK OFFICE
CERTIFICATE OF CORRECTION

PATENT NO. : 6,982,026 B2
APPLICATION NO. : 09/809649
DATED : January 3, 2006
INVENTOR(S) : Michael Charles Milner Cockrem and Istvan Kovacs It is certified that error appears in the above-identified patent and that said Letters Patent is hereby corrected as shown below:

Column 45, line 23 through Column 46, line 26 (cont'd),
and insert the following:
-- 58. The process of claim 1, wherein the at least one azeotroping agent is an ether having from 7 to 16 carbon atoms or an alcohol having from 7 to 13 carbon atoms. --.

Signed and Sealed this

Eleventh Day of July, 2006

JON W. DUDAS
*Director of the United States Patent and Trademark Office*